United States Patent
Ørts et al.

(10) Patent No.: US 11,786,226 B2
(45) Date of Patent: *Oct. 17, 2023

(54) SINGLE INSERTION MULTIPLE SAMPLE BIOPSY APPARATUS

(71) Applicant: C. R. Bard, Inc., Franklin Lakes, NJ (US)

(72) Inventors: Søren Falkesgaard Ørts, Virum (DK); Angela K. Jensen, Phoenix, AZ (US); Jens Jørgen Holme, Lyngby (DK); Weinan Ji, Lillerød (DK); Marek Fraczkowski, Szczecin (PL)

(73) Assignee: C.R. Bard, Inc., Franklin Lakes, NJ (US)

( * ) Notice: Subject to any disclaimer, the term of this patent is extended or adjusted under 35 U.S.C. 154(b) by 441 days.

This patent is subject to a terminal disclaimer.

(21) Appl. No.: 17/168,441

(22) Filed: Feb. 5, 2021

(65) Prior Publication Data

US 2021/0177387 A1 Jun. 17, 2021

Related U.S. Application Data

(63) Continuation of application No. 16/349,334, filed as application No. PCT/US2017/062961 on Nov. 22, 2017, now Pat. No. 10,945,713.

(60) Provisional application No. 62/425,974, filed on Nov. 23, 2016.

(51) Int. Cl.
 *A61B 10/02* (2006.01)

(52) U.S. Cl.
 CPC ...... *A61B 10/0275* (2013.01); *A61B 10/0283* (2013.01); *A61B 2010/0208* (2013.01); *A61B 2010/0225* (2013.01)

(58) Field of Classification Search
 CPC .......... A61B 10/02–06; A61B 2010/0208–045
 See application file for complete search history.

(56) References Cited

U.S. PATENT DOCUMENTS

| | | |
|---|---|---|
| 3,800,783 A | 4/1974 | Jamshidi |
| 3,929,123 A | 12/1975 | Jamshidi |
| 4,517,965 A | 5/1985 | Ellison |
| 5,031,634 A | 7/1991 | Simon |
| 5,125,521 A | 6/1992 | Somogyi |
| 5,148,813 A | 9/1992 | Bucalo |
| 5,201,716 A | 4/1993 | Richard |
| 5,601,585 A * | 2/1997 | Banik ............... A61B 10/06 606/209 |
| 5,634,918 A | 6/1997 | Richards |

(Continued)

FOREIGN PATENT DOCUMENTS

| | | |
|---|---|---|
| CN | 1700887 A | 11/2005 |
| CN | 1799513 A | 7/2006 |

(Continued)

OTHER PUBLICATIONS

Office Action dated Aug. 3, 2021 corresponding to Chinese Paten Application 201780080429.8.

*Primary Examiner* — David J. McCrosky
(74) *Attorney, Agent, or Firm* — Dinsmore & Shohl LLP

(57) ABSTRACT

A method of using a biopsy apparatus includes moving a stylet cannula relative to a vacuum cannula between a first extended position and a first retracted position; and receiving a protrusion member within a flared portion of the vacuum cannula when the stylet cannula is in the first retracted position.

20 Claims, 11 Drawing Sheets

(56) References Cited

U.S. PATENT DOCUMENTS

| | | |
|---|---|---|
| 5,794,626 A | 8/1998 | Kieturakis |
| 5,857,981 A | 1/1999 | Bucalo et al. |
| 5,959,433 A | 9/1999 | Rohde |
| 6,238,355 B1 | 5/2001 | Daum |
| 6,312,429 B1 | 11/2001 | Burbank et al. |
| 6,416,484 B1 | 7/2002 | Miller et al. |
| D463,555 S | 9/2002 | Etter et al. |
| 6,497,706 B1 | 12/2002 | Burbank et al. |
| 6,551,253 B2 | 4/2003 | Worm et al. |
| 6,607,528 B1 | 8/2003 | Quick et al. |
| D491,268 S | 6/2004 | Hickingbotham |
| D497,427 S | 10/2004 | Hickingbotham |
| 6,870,475 B2 | 3/2005 | Fitch et al. |
| 6,872,185 B2 | 3/2005 | Fisher |
| D535,748 S | 1/2007 | Wolf |
| 7,189,206 B2 | 3/2007 | Quick et al. |
| 7,456,606 B1 | 11/2008 | Legg |
| 7,488,295 B2 | 2/2009 | Burbank et al. |
| 7,654,997 B2 * | 2/2010 | Makower ............... A61B 10/06 604/509 |
| 7,952,322 B2 | 5/2011 | Partovi et al. |
| D643,531 S | 8/2011 | van der Weiden |
| 8,002,732 B2 | 8/2011 | Visconti |
| 8,169,185 B2 | 5/2012 | Partovi et al. |
| 8,207,906 B2 | 6/2012 | Tiscareno et al. |
| 8,282,321 B2 | 10/2012 | Thiel |
| 8,298,213 B2 | 10/2012 | Singh |
| 8,413,811 B1 | 4/2013 | Arendt |
| 8,629,654 B2 | 1/2014 | Partovi et al. |
| 8,696,674 B2 | 4/2014 | Howard et al. |
| 8,702,623 B2 | 4/2014 | Parihar et al. |
| 8,845,546 B2 | 9/2014 | Speeg et al. |
| 9,000,720 B2 | 4/2015 | Stulen et al. |
| 9,072,506 B1 | 7/2015 | Seiger et al. |
| 9,101,347 B2 | 8/2015 | McGhie et al. |
| 9,107,691 B2 | 8/2015 | Fojtik |
| 9,155,527 B2 | 10/2015 | Vetter et al. |
| 9,178,369 B2 | 11/2015 | Partovi |
| 9,381,058 B2 | 7/2016 | Houser et al. |
| 9,421,062 B2 | 8/2016 | Houser et al. |
| 9,496,732 B2 | 11/2016 | Partovi |
| 9,717,482 B2 | 8/2017 | Fiebig et al. |
| D802,763 S | 11/2017 | Sweitzer |
| 9,909,103 B2 | 3/2018 | Howard et al. |
| 2002/0019596 A1 | 2/2002 | Eggers et al. |
| 2005/0113716 A1 | 5/2005 | Mueller, Jr. et al. |
| 2006/0108977 A1 | 5/2006 | Kagermeier et al. |
| 2006/0173377 A1 | 8/2006 | Mccullough et al. |
| 2009/0079386 A1 | 3/2009 | Gallagher et al. |
| 2009/0171147 A1 | 7/2009 | Lee et al. |
| 2011/0071432 A1 | 3/2011 | Carrillo, Jr. et al. |
| 2013/0020201 A1 | 1/2013 | Yotoriyama et al. |
| 2014/0191709 A1 | 7/2014 | Celentano et al. |
| 2014/0276665 A1 | 9/2014 | Lopez et al. |
| 2015/0025415 A1 | 1/2015 | Videbaek et al. |
| 2016/0038127 A1 | 2/2016 | Hashimshony |
| 2016/0199150 A1 | 7/2016 | Field et al. |
| 2016/0256138 A1 | 9/2016 | Videbaek et al. |
| 2018/0000463 A1 | 1/2018 | Keller |

FOREIGN PATENT DOCUMENTS

| | | |
|---|---|---|
| CN | 101125093 A | 2/2008 |
| CN | 101125093 A | 2/2008 |
| CN | 101237822 A | 8/2008 |
| CN | 101877564 A | 11/2010 |
| CN | 102036849 A | 4/2011 |
| CN | 102307529 A | 1/2012 |
| CN | 102348418 A | 2/2012 |
| CN | 102639066 A | 8/2012 |
| CN | 103037762 A | 4/2013 |
| CN | 103281970 A | 9/2013 |
| CN | 104703549 A | 6/2015 |
| CN | 106028799 A | 10/2016 |
| EP | 1698282 A1 | 9/2006 |
| EP | 1815798 A2 | 8/2007 |
| EP | 1965190 A1 | 9/2008 |
| JP | 2006305260 A | 11/2006 |
| WO | 2004075728 A2 | 9/2004 |
| WO | 2005070470 A1 | 8/2005 |
| WO | 2007021905 A2 | 2/2007 |
| WO | 2016178656 A1 | 11/2016 |

* cited by examiner

SINGLE INSERTION MULTIPLE SAMPLE BIOPSY APPARATUS

CROSS-REFERENCE TO RELATED APPLICATIONS

This application is a continuation of U.S. patent application Ser. No. 16/349,334, filed May 13, 2019, which is a U.S. national phase of International Application No. PCT/US2017/062961, filed Nov. 22, 2017, which claims priority to U.S. provisional patent application Ser. No. 62/425,974 filed Nov. 23, 2016, each of which is incorporated herein by reference.

TECHNICAL FIELD

The present invention relates to biopsy devices, and, more particularly, to a single insertion multiple sample biopsy apparatus.

BACKGROUND ART

A biopsy may be performed on a patient to help in determining whether the tissue in a region of interest includes cancerous cells. One biopsy technique used to evaluate breast tissue, for example, involves inserting a biopsy probe into the breast tissue region of interest to capture one or more tissue samples from the region. Such a biopsy technique often utilizes a vacuum to pull the tissue to be sampled into a sample notch of the biopsy probe, after which the tissue is severed and collected. Efforts continue in the art to improve the ability of the biopsy device to sever a tissue sample, and to transport the severed tissue sample to a sample collection container.

What is needed in the art is a biopsy device that has the ability to promote effective severing of a tissue sample and effective transport of the tissue sample to a sample collection container.

SUMMARY OF INVENTION

The present invention provides a biopsy device that has the ability to promote effective severing of a tissue sample and effective transport of the tissue sample to a sample collection container.

The invention in one form is directed to a biopsy apparatus that includes a driver assembly and a biopsy probe assembly. The driver assembly has an electromechanical power source and a vacuum source. The biopsy probe assembly is releasably attached to the driver assembly. The biopsy probe assembly has a vacuum cannula and a stylet cannula coaxially arranged along a longitudinal axis, with the vacuum cannula being positioned inside the stylet cannula. The vacuum cannula is coupled in fluid communication with the vacuum source. The vacuum cannula has an elongate portion and a flared portion that extends distally from the elongate portion. The stylet cannula is coupled in driving communication with the electromechanical power source. The stylet cannula is movable relative to the vacuum cannula between a first extended position and a first retracted position. The stylet cannula has a proximal portion and a distal portion. The distal portion has a sample notch and a protrusion member that extends proximally in a lumen of the stylet cannula along a portion of a longitudinal extent of the sample notch, wherein when the stylet cannula is in the first retracted position, the protrusion member is received within the flared portion of the vacuum cannula.

The biopsy apparatus may further include a controller circuit that has a virtual energy reservoir, and the controller circuit executes program instructions to control current to motors when engaging dense tissue.

The invention in another form is directed to a biopsy apparatus that includes a driver assembly and a biopsy probe assembly. The driver assembly has an electromechanical power source, a vacuum source, and a controller circuit. The controller circuit is electrically and communicatively coupled to the electromechanical power source and to the vacuum source. The biopsy probe assembly is releasably attached to the driver assembly. The biopsy probe assembly has a vacuum cannula, a stylet cannula, and a cutter cannula coaxially arranged along a longitudinal axis. The vacuum cannula is positioned inside the stylet cannula, and the stylet cannula is positioned inside the cutter cannula. The vacuum cannula is coupled in fluid communication with the vacuum source. The vacuum cannula has an elongate portion and a flared portion that extends distally from the elongate portion. The stylet cannula is coupled in driving communication with the electromechanical power source. The stylet cannula is movable relative to the vacuum cannula between a first extended position and a first retracted position. The stylet cannula has a proximal portion and a distal portion. The distal portion has a sample notch and a protrusion member that extends proximally in a lumen of the stylet cannula along a portion of a longitudinal extent of the sample notch. When the stylet cannula is in the retracted position, the protrusion member of the stylet cannula is received within the flared portion of the vacuum cannula. The cutter cannula is coupled in driving communication with the electromechanical power source. The cutter cannula is movable relative to the stylet cannula between a second extended position to cover the sample notch and a second retracted position to expose the sample notch when the stylet cannula is in the first extended position.

BRIEF DESCRIPTION OF DRAWINGS

The above-mentioned and other features and advantages of this invention, and the manner of attaining them, will become more apparent and the invention will be better understood by reference to the following description of an embodiment of the invention taken in conjunction with the accompanying drawings, wherein.

Corresponding reference characters indicate corresponding parts throughout the several views. The exemplifications set out herein illustrate at least one embodiment of the invention, and such exemplifications are not to be construed as limiting the scope of the invention in any manner.

DESCRIPTION OF EMBODIMENTS

Figure 1:
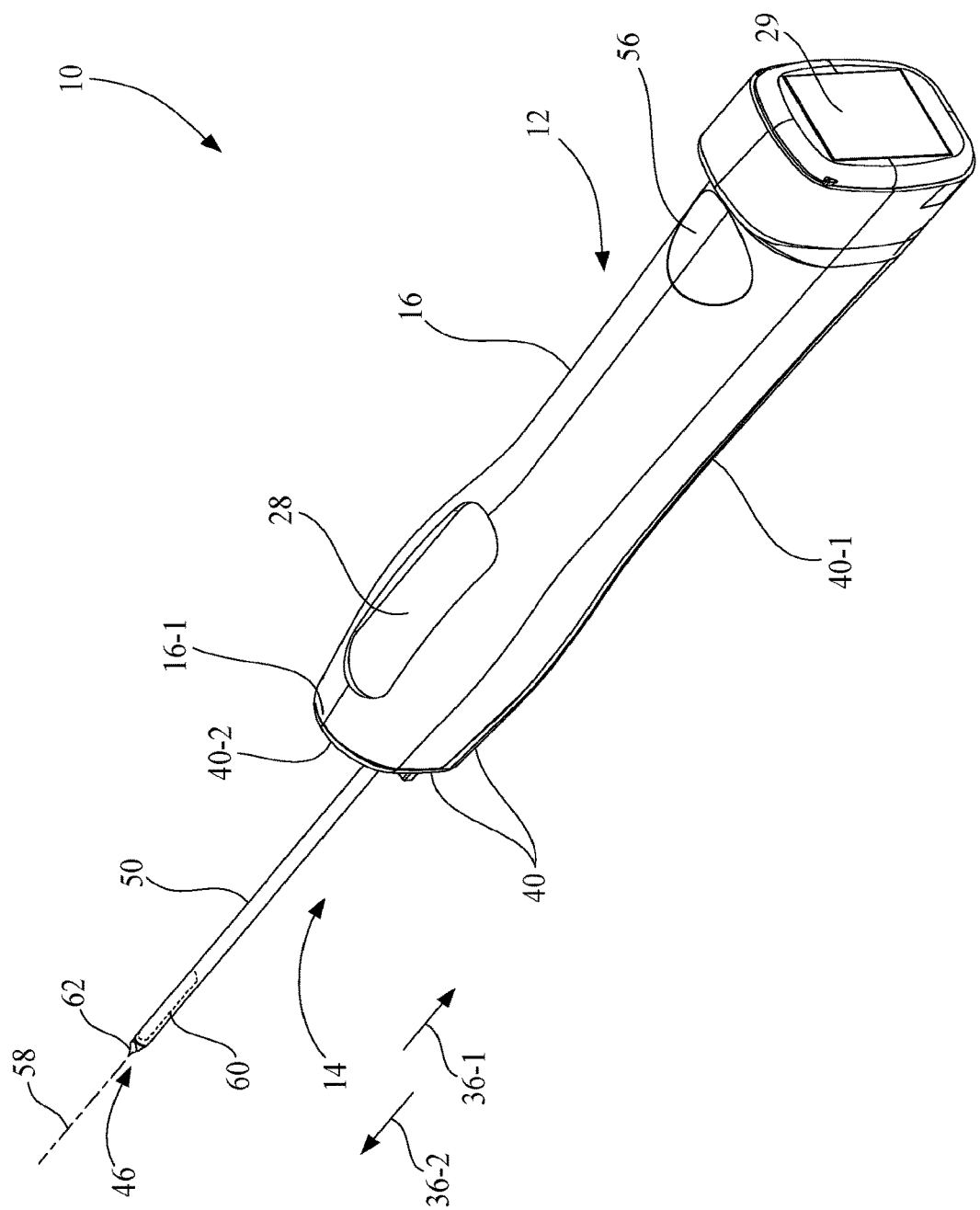
FIG. 1 is a perspective view of a biopsy apparatus configured in accordance with an embodiment of the present invention, with a biopsy probe assembly attached to a driver assembly.
Figure 2:
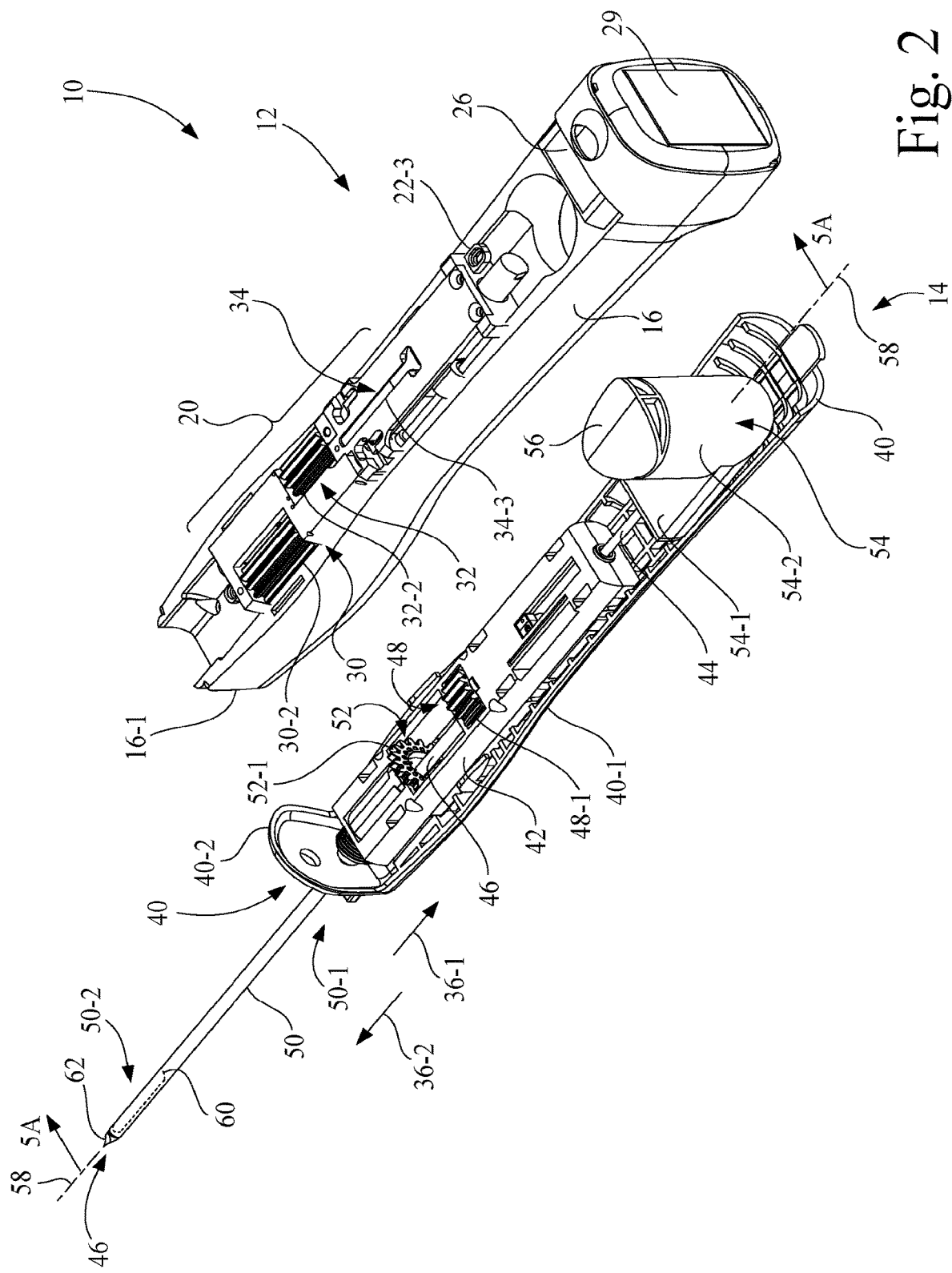
FIG. 2 is a perspective view of the biopsy apparatus of FIG. 1, with the biopsy probe assembly detached from the driver assembly and with the driver assembly inverted to expose the drive features of the driver assembly.

Referring now to the drawings, and more particularly to FIGS. 1 and 2, there is shown a biopsy apparatus 10 which generally includes a non-invasive, e.g., non-disposable, driver assembly 12 and an invasive, e.g., disposable, biopsy probe assembly 14. As used herein, the term "non-disposable" is used to refer to a device that is intended for use on multiple patients during the lifetime of the device, and the term "disposable" is used to refer to a device that is intended to be disposed of after use on a single patient. Driver assembly 12 includes a driver housing 16 that is configured and ergonomically designed to be grasped by a user.

Figure 3:
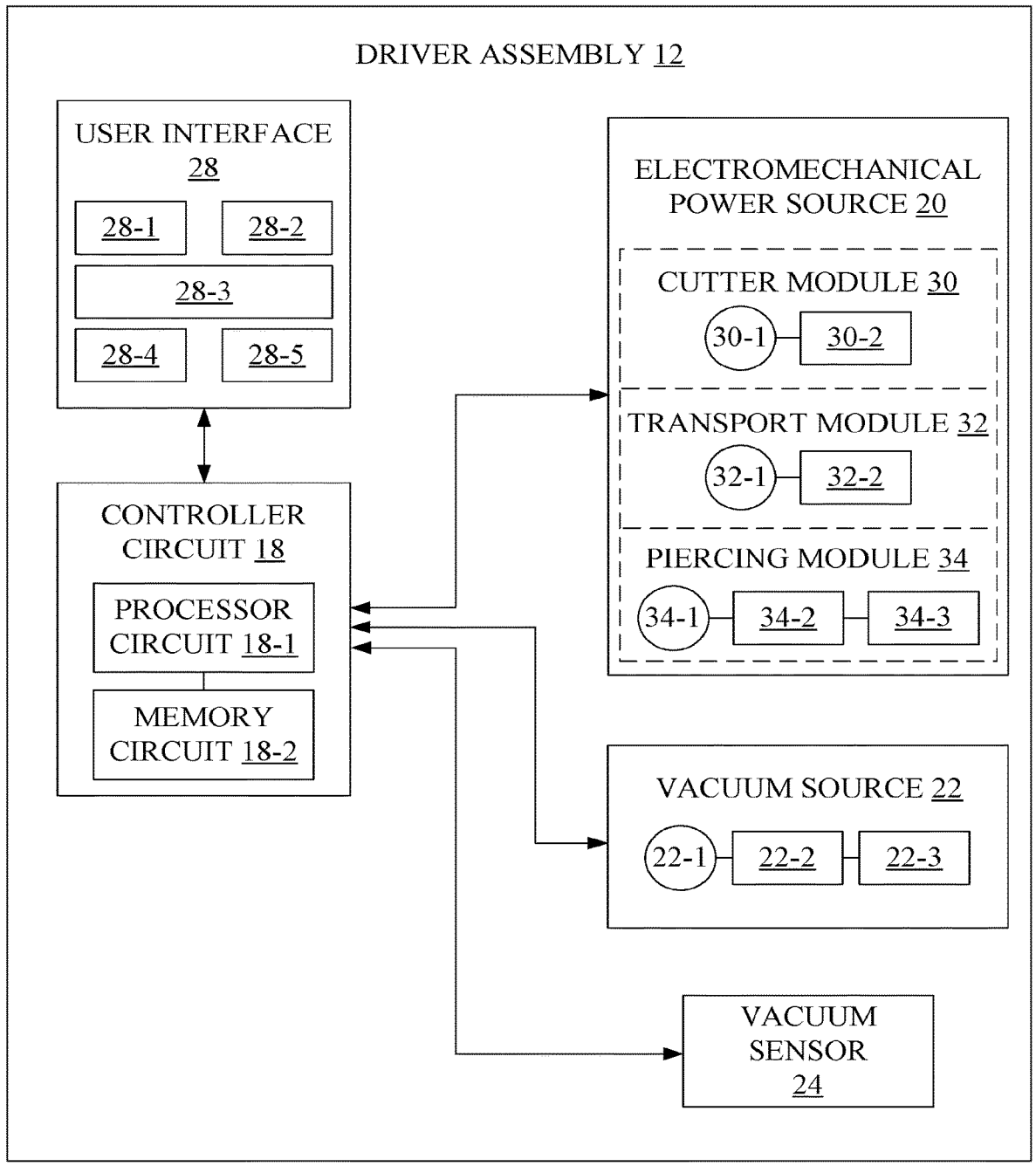
FIG. 3 is a block representation of the driver assembly of FIG. 1.

Referring to FIGS. 2 and 3, driver assembly 12 includes within driver housing 16 a controller circuit 18, an electromechanical power source 20, a vacuum source 22, a vacuum sensor 24, and a battery 26 (or alternatively an AC adapter). A user interface 28 (see FIG. 1), such as a keypad, is located to be mounted to driver housing 16, and externally accessible by the user with respect to driver housing 16. Battery 26 may be, for example, a rechargeable battery, which may be charged by an inductive charging device coupled to inductive coil 29, or alternatively, by an electrical connection to an electrical power supply. Battery 26 is electrically coupled to controller circuit 18, electromechanical power source 20, vacuum source 22, and user interface 28.

Referring to FIG. 3, user interface 28 may include control buttons and visual/aural indicators, with the control buttons providing user control over various functions of biopsy apparatus 10, and with the visual/aural indicators providing visual/aural feedback of the status of one or more conditions and/or positions of components of biopsy apparatus 10. The control buttons may include a sample button 28-1 and a prime/pierce button 28-2. The visual indicators may include a display screen 28-3 and/or one or more light emitting diodes (LED) 28-4. The aural indicator may include a buzzer 28-5. The control buttons may include tactile feedback to the user when activated.

Controller circuit 18 is electrically and communicatively coupled to electromechanical power source 20, vacuum source 22, vacuum sensor 24, and user interface 28, such as by one or more wires or circuit traces. Controller circuit 18 may be assembled on an electrical circuit board, and includes, for example, a processor circuit 18-1 and a memory circuit 18-2.

Processor circuit 18-1 has one or more programmable microprocessors and associated circuitry, such as an input/output interface, clock, buffers, memory, etc. Memory circuit 18-2 is communicatively coupled to processor circuit 18-1, e.g., via a bus circuit, and is a non-transitory electronic memory that may include volatile memory circuits, such as random access memory (RAM), and non-volatile memory circuits, such as read only memory (ROM), electronically erasable programmable ROM (EEPROM), NOR flash memory, NAND flash memory, etc. Controller circuit 18 may be formed as one or more Application Specific Integrated Circuits (ASIC).

Controller circuit 18 is configured via software and/or firmware residing in memory circuit 18-2 to execute program instructions to perform functions associated with the retrieval of biopsy tissue samples, such as that of controlling and/or monitoring one or more components of electromechanical power source 20, vacuum source 22, and vacuum sensor 24.

Electromechanical power source 20 may include, for example, a cutter module 30, a transport module 32, and a piercing module 34, each being respectively electrically coupled to battery 26. Each of cutter module 30, transport module 32, and piercing module 34 is electrically and controllably coupled to controller circuit 18 by one or more electrical conductors, e.g., wires or circuit traces.

Cutter module 30 may include an electrical motor 30-1 having a shaft to which a drive gear 30-2 is attached. Transport module 32 may include an electrical motor 32-1 having a shaft to which a drive gear 32-2 is attached. Piercing module 34 may include an electrical motor 34-1, a drive spindle 34-2, and a piercing shot drive 34-3. Each electrical motor 30-1, 32-1, 34-1 may be, for example, a direct current (DC) motor or stepper motor. As an alternative to the arrangement described above, each of cutter module 30, transport module 32, and piercing module 34 may include one or more of a gear, gear train, belt/pulley arrangement, etc., interposed between the respective motor and drive gear or drive spindle.

Piercing module 34 is configured such that an activation of electrical motor 34-1 and a drive spindle 34-2 causes a piercing shot drive 34-3 to move in a proximal direction 36-1 to compress a firing spring, e.g., one or more coil springs, and to latch piercing shot drive 34-3 in a ready position. Upon actuation of prime/pierce button 28-2 of user interface 28, piercing shot drive 34-3 is propelled, i.e., fired, in a distal direction 36-2 (see FIG. 2).

Vacuum source 22 is electrically and controllably coupled to battery 26 by one or more electrical conductors, e.g., wires or circuit traces. Vacuum source 22 may include, for example, an electric motor 22-1 that drives a vacuum pump 22-2. Vacuum source 22 has a vacuum source port 22-3 coupled to vacuum pump 22-2 for establishing vacuum in biopsy probe assembly 14. Electric motor 22-1 may be, for example, a rotary, linear or vibratory DC motor. Vacuum pump 22-2 may be, for example, a peristaltic pump or a diaphragm pump, or one or more of each connected in series or parallel.

Vacuum sensor 24 is electrically coupled to controller circuit 18 by one or more electrical conductors, e.g., wires or circuit traces. Vacuum sensor 24 may be a pressure differential sensor that provides vacuum (negative pressure) feedback signals to controller circuit 18. In some implementations, vacuum sensor 24 may be incorporated into vacuum source 22.

Referring to FIGS. 1 and 2, biopsy probe assembly 14 is configured for releasable attachment to driver assembly 12. As used herein, the term "releasable attachment" means a configuration that facilitates an intended temporary connection followed by selective detachment involving a manipulation of disposable biopsy probe assembly 14 relative to driver assembly 12, without the need for tools.

Figure 4:
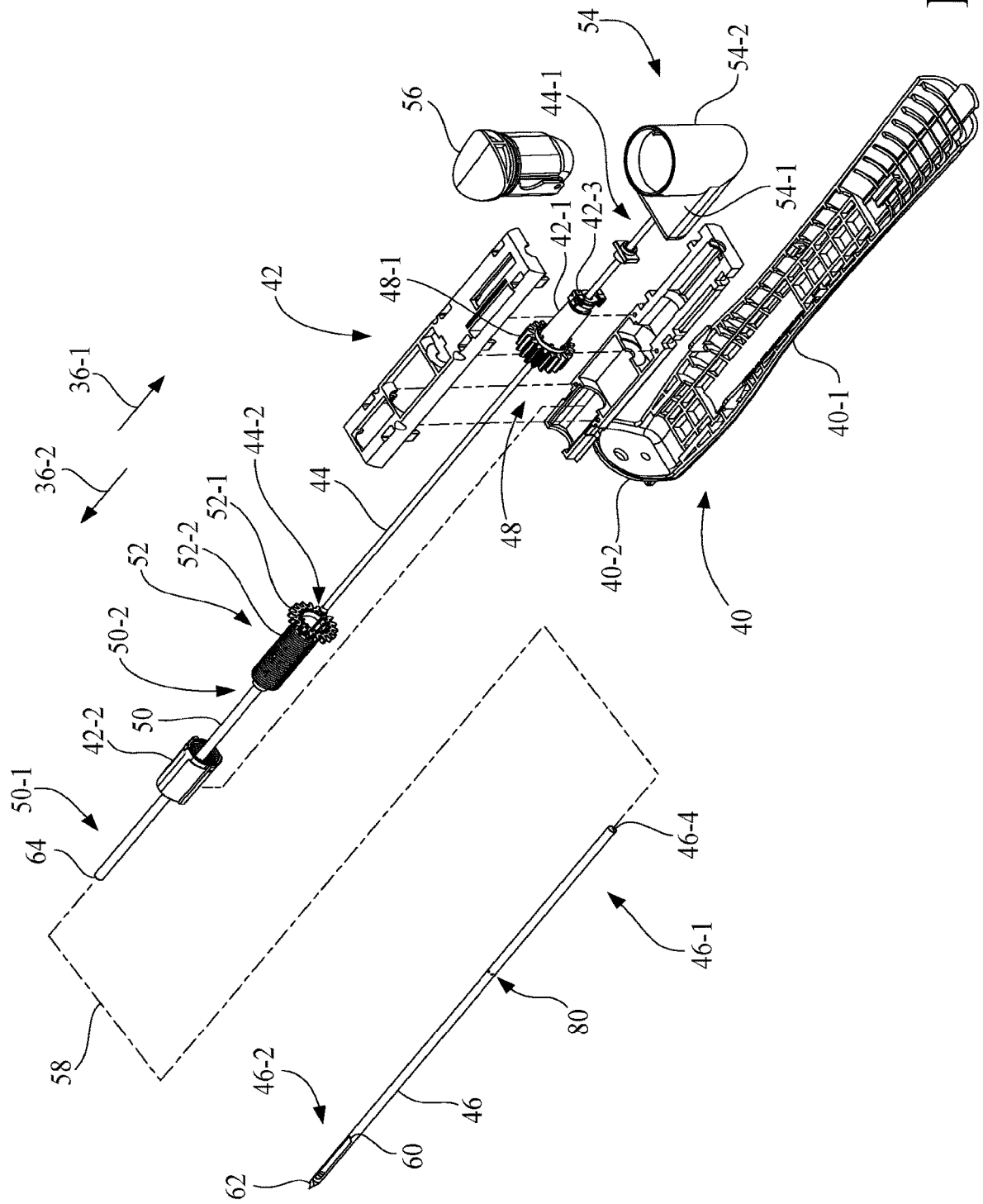
FIG. 4 is an exploded view of the biopsy probe assembly of FIG. 1.

Referring to the exploded view of FIG. 4, biopsy probe assembly 14 includes a probe housing 40, a probe sub-housing 42, a vacuum cannula 44, a stylet cannula 46, a stylet gear-spindle set 48 for linear stylet translation, a cutter cannula 50, a cutter gear-spindle set 52 for rotary and linear cutter translation, a sample manifold 54, and a sample cup 56.

Figure 5A:
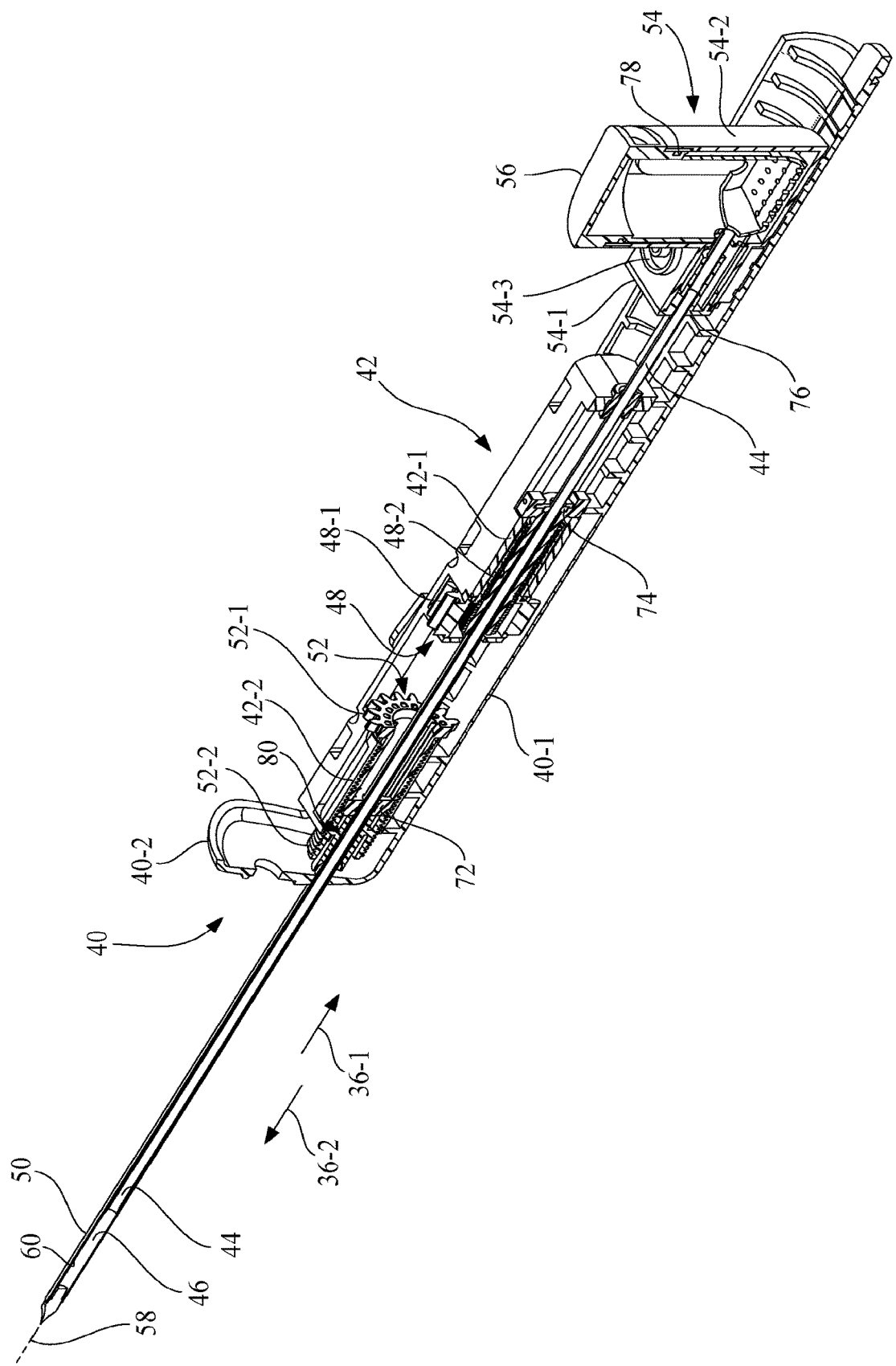
FIG. 5A is a section view of the biopsy probe assembly of FIG. 1, taken along line 5A-5A of FIG. 2.

Referring to FIGS. 2, 4, and 5A, probe housing 40 is formed as an L-shaped structure having an elongate portion 40-1 and a front plate 40-2. When biopsy probe assembly 14 is attached to driver assembly 12, front plate 40-2 is positioned distally adjacent to an entirety of front surface 16-1 of driver housing 16, i.e., so as to shield the entirety of front surface 16-1 of the non-disposable driver assembly from contact with a patient.

Vacuum cannula 44, stylet cannula 46, and cutter cannula 50 are coaxially arranged along a longitudinal axis 58 in a nested tube arrangement, with vacuum cannula 44 being the innermost tube, cutter cannula 50 being the outermost tube, and stylet cannula 46 being the intermediate tube that is interposed between vacuum cannula 44 and cutter cannula 50. In other words, vacuum cannula 44 is positioned inside stylet cannula 46, and stylet cannula 46 is positioned inside cutter cannula 50.

Vacuum cannula 44 is mounted to be stationary relative to probe sub-housing 42. Vacuum cannula 44 is coupled in fluid communication with vacuum source 22 via sample manifold 54.

Figure 5B:
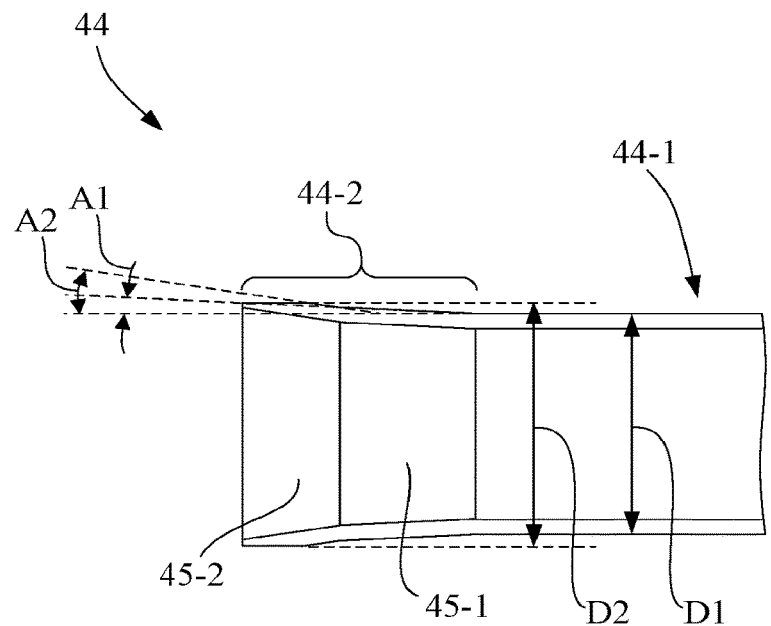
FIG. 5B is an enlarged portion of the vacuum cannula depicted in FIG. 5A.

Referring to FIGS. 4, 5A, and 5B, vacuum cannula 44 includes an elongate portion 44-1 and a flared portion 44-2 that extends distally from elongate portion 44-1. Elongate portion 44-1 has a first outside diameter D1. Flared portion 44-2 flares from elongate portion 44-1 in two stages, namely, a first flared stage 45-1 and a second flared stage 45-2. First flared stage 45-1 diverges from elongate portion 44-1 at a first acute angle A1, and second flared stage 45-2 diverges from first flared stage 45-1 at a second acute angle A2 relative to elongate portion 44-1, with acute angle A2 being larger than acute angle A1. A distal outside diameter D2 of second flared stage 45-2 is selected to be accommodated within, and in sliding contact with, lumen 46-4 of stylet cannula 46. Each of first flared stage 45-1 and second flared stage 45-2 of flared portion 44-2 has a distally and gradually increasing diameter, which is larger than the diameter D1 of elongate portion 44-1.

Referring again to FIG. 4, stylet cannula 46 includes a proximal portion 46-1 and a distal portion 46-2. Distal portion 46-2 includes a sample notch 60. Attached to distal portion 46-2 is a piercing tip 62, which in turn forms part of stylet cannula 46. Stylet gear-spindle set 48 threadably engages a transport spindle 42-3 is fixedly attached (e.g., glued, welded or staked) to proximal portion 46-1 of stylet cannula 46. Stylet gear-spindle set 48 is a unitary gear having a driven gear 48-1 fixedly attached to a threaded spindle 48-2, and may be formed as a single molded component. Stylet cannula 46 is retracted or extended along longitudinal axis 58 by activation of transport module 32 of biopsy probe assembly 14, with drive gear 32-2 of transport module 32 of driver assembly 12 being engaged with driven gear 48-1 of stylet gear-spindle set 48.

Figure 5C:
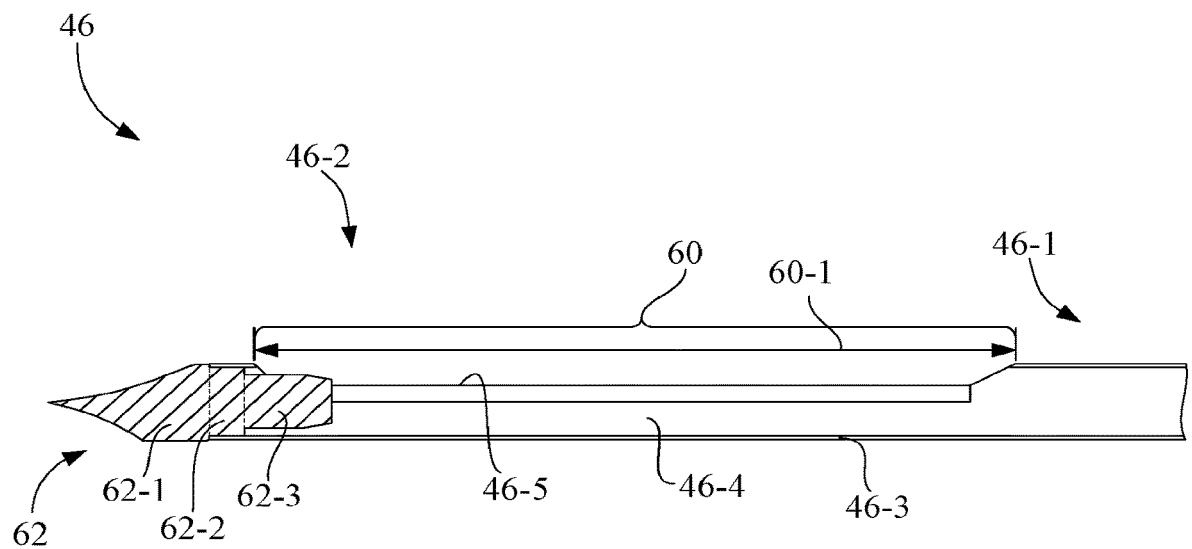
FIG. 5C is an enlarged portion of the stylet cannula depicted in FIG. 5A.
Figure 6A:
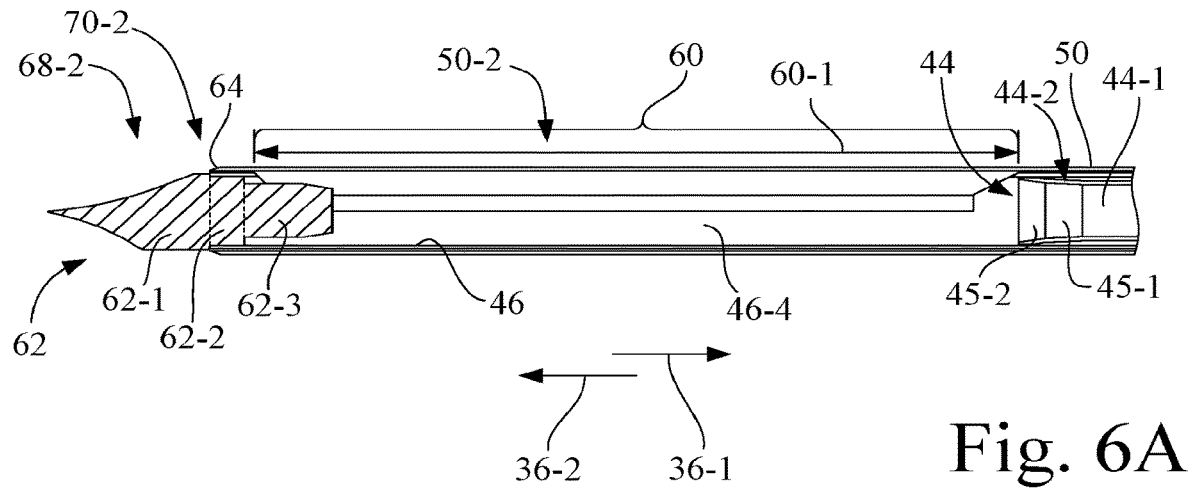
FIG. 6A shows the relative positions of the vacuum cannula, the stylet cannula, and the cutter cannula before, during, and immediately after a piercing shot.
Figure 6B:
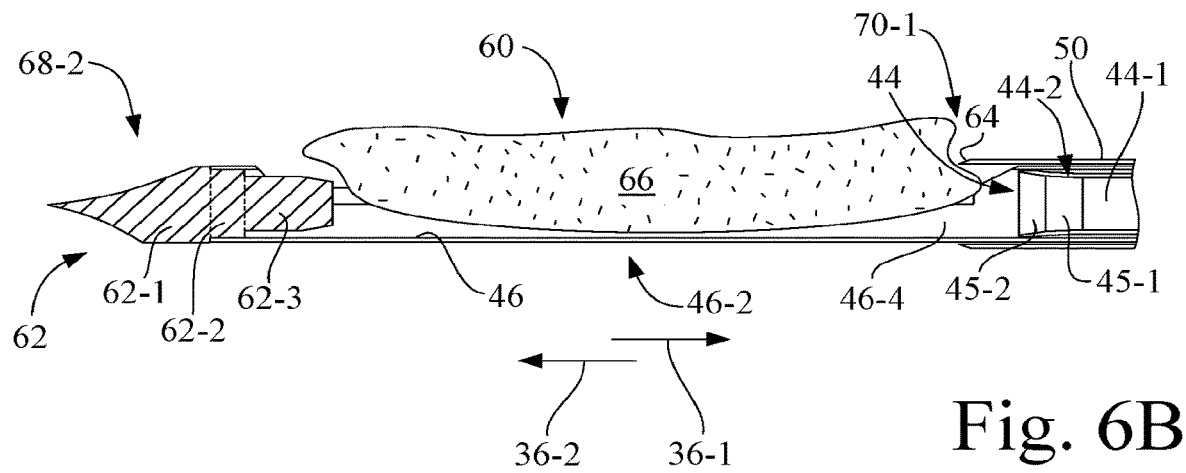
FIG. 6B shows the relative positions of the vacuum cannula, the stylet cannula, and the cutter cannula, and with the cutter cannula retracted to expose the sample notch of the stylet cannula.

Referring also to FIGS. 5C, 6A, and 6B, sample notch 60 is formed as an elongate opening in a side wall 46-3 of stylet cannula 46 to facilitate a reception of tissue 66 into a lumen 46-4 of stylet cannula 46. Sample notch 60 has a longitudinal extent 60-1 that extends along longitudinal axis longitudinal axis 58. Sample notch 60 does not extend in side wall 46-3 below a centerline of the diameter of stylet cannula 46, and may include cutting edges around the perimeter of the opening formed by sample notch 60, wherein the cutting edges of the elongate (linear) portions of sample notch 60 each have a cutting edge 46-5 that diverges from a cutting edge along the side wall 46-3 to the centerline at a diameter of stylet cannula 46.

Piercing tip 62 has a tip portion 62-1, a mounting portion 62-2, and a protrusion member 62-3. Piercing tip 62 is inserted into lumen 46-4 of stylet cannula 46 at distal portion 46-2, with mounting portion 62-2 being attached to distal portion 46-2 of stylet cannula 46, such as an adhesive or weld. As such, tip portion 62-1 extends distally from distal portion 46-2 of stylet cannula 46, and protrusion member 62-3 extends proximally (i.e., in proximal direction 36-1) in lumen 46-4 along a portion of the longitudinal extent 60-1 of sample notch 60. Accordingly, as depicted in FIGS. 6E and 6G, when stylet cannula 46 is fully retraced in the proximal direction 36-1, protrusion member 62-3 is received into flared portion 44-2 of vacuum cannula 44. At least the proximal tip portion of protrusion member 62-3 has a proximally decreasing diameter.

Referring again to FIG. 4, cutter cannula 50 includes a proximal portion 50-1 and a distal portion 50-2. Distal portion 50-2 includes an annular cutting edge 64. Cutter gear-spindle set 52 is fixedly attached (e.g., glued, welded or staked) to proximal portion 50-1 of cutter cannula 50. Cutter gear-spindle set 52 is a unitary gear having a driven gear 52-1 fixedly attached to a threaded spindle 52-2, and may be formed as a single molded component. Cutter cannula 50 is retracted or extended along longitudinal axis 58 by activation of cutter module 30 of biopsy probe assembly 14, with drive gear 30-2 of cutter module 30 of driver assembly 12 being engaged with driven gear 52-1 of cutter gear-spindle set 52. Thus, cutter cannula 50 has a rotational cutting motion and is translated axially along longitudinal axis 58. The pitch of the threads of threaded spindle 52-2 determines the number of revolutions per axial distance (in millimeters (mm)) that cutter cannula 50 moves axially.

Referring to FIGS. 4 and 5A, sample manifold 54 is configured as an L-shaped structure having a vacuum chamber portion 54-1 and a collection chamber portion 54-2. Vacuum chamber portion 54-1 includes a vacuum input port 54-3 that is arranged to sealably engage vacuum source port 22-3 of vacuum source 22 of driver assembly 12 when biopsy probe assembly 14 is attached to driver assembly 12. Vacuum chamber portion 54-1 is connected in fluid communication with collection chamber portion 54-2. Proximal end of elongate portion 44-1 of vacuum cannula 44 passes through vacuum chamber portion 54-1 and is in direct fluid communication with collection chamber portion 54-2. Collection chamber portion 54-2 has a cavity sized and arranged to removably receive sample cup 56, such that sample cup 56 is in direct fluid communication with elongate portion 44-1 of vacuum cannula 44, and sample cup 56 also is in direct fluid communication with vacuum input port 54-3 of vacuum chamber portion 54-1. Blotting papers are placed in vacuum chamber portion 54-1 in a region between vacuum input port 54-3 and collection chamber portion 54-2.

Accordingly, a tissue sample severed by cutter cannula 50 at sample notch 60 of stylet cannula 46 may be transported by vacuum applied by vacuum source 22 at sample cup 56, through vacuum cannula 44, and into sample cup 56.

Referring again to FIGS. 2, 4 and 5A, probe sub-housing 42 is a sub-housing that is slidably coupled to probe housing 40, e.g., using a rail/slot arrangement. Probe sub-housing 42 includes a proximal threaded portion 42-1 and a distal threaded portion 42-2.

Proximal threaded portion 42-1 in probe sub-housing 42 has a threaded hole that threadably receives threaded spindle 48-2 of stylet gear-spindle set 48, such that rotation of driven gear 48-1 of stylet gear-spindle set 48 results in a linear translation of stylet cannula 46 along longitudinal axis 58, with a direction of rotation correlating to a direction of translation of stylet cannula 46 in one of proximal direction 36-1 and distal direction 36-2. Driven gear 48-1 of stylet gear-spindle set 48 engages drive gear 32-2 of transport module 32 when biopsy probe assembly 14 is attached to driver assembly 12 (see FIG. 1).

Likewise, distal threaded portion 42-2 of probe sub-housing 42 has a threaded hole that threadably receives threaded spindle 52-2 of cutter gear-spindle set 52, such that rotation of driven gear 52-1 of cutter gear-spindle set 52 results in a combined rotation and linear translation of cutter cannula 50 along longitudinal axis 58, with a direction of rotation correlating to a direction of translation of cutter cannula 50. Driven gear 52-1 of cutter gear-spindle set 52 engages drive gear 30-2 of cutter module 30 when biopsy probe assembly 14 is attached to driver assembly 12 (see FIG. 1).

Also, when biopsy probe assembly 14 is attached to driver assembly 12, referring also to FIGS. 2 and 3, probe sub-housing 42 is connected to piercing shot drive 34-3 of piercing module 34. As such, upon a first actuation of prime/pierce button 28-2, probe sub-housing 42 and piercing shot drive 34-3 are translated in unison in proximal direction 36-1 to position piercing shot drive 34-3 and probe sub-housing 42 carrying stylet cannula 46 and cutter cannula 50 in the ready, i.e., cocked position, and upon a second actuation of prime/pierce button 28-2 to effect a piercing shot, probe sub-housing 42 and piercing shot drive 34-3 are rapidly propelled in unison in distal direction 36-2 to position stylet cannula 46 and cutter cannula 50 at the distal most position of the combined elements, e.g., within the patient.

Figure 6C:
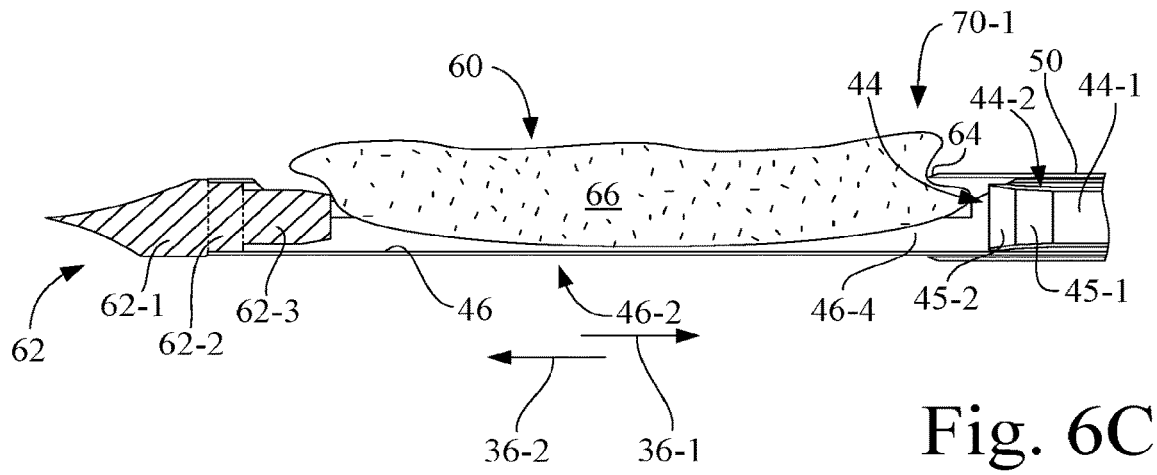
FIG. 6C shows the relative positions of the vacuum cannula, the stylet cannula, and the cutter cannula, depicting a shaking of the sample notch by alternatingly moving the stylet cannula in the proximal direction and in the distal direction for a short distance.
Figure 6D:
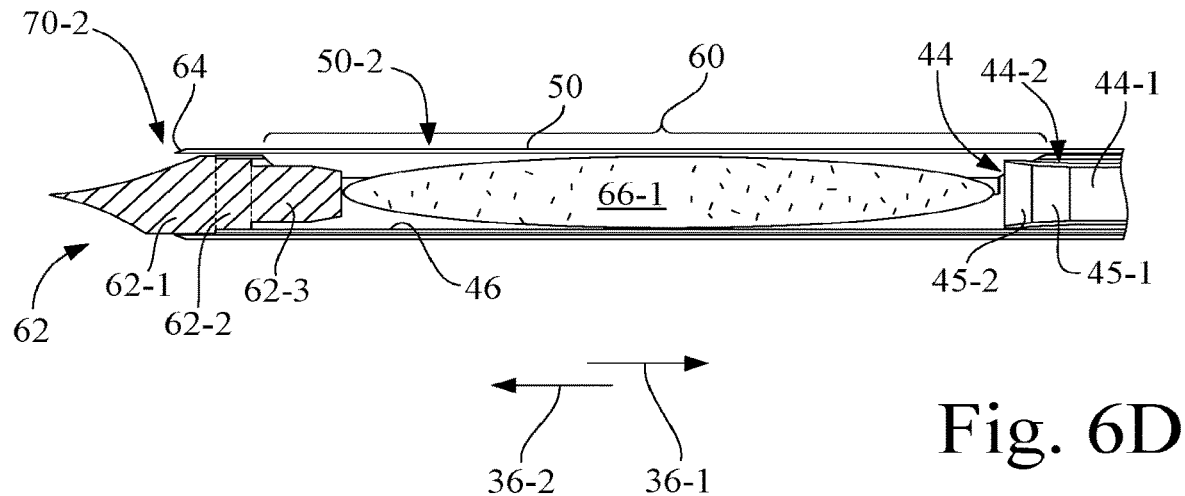
FIG. 6D shows the relative positions of the vacuum cannula, the stylet cannula, and the cutter cannula, wherein the cutter cannula is rotated and translated in the distal direction to sever a tissue sample from the tissue received in the sample notch.
Figure 6E:
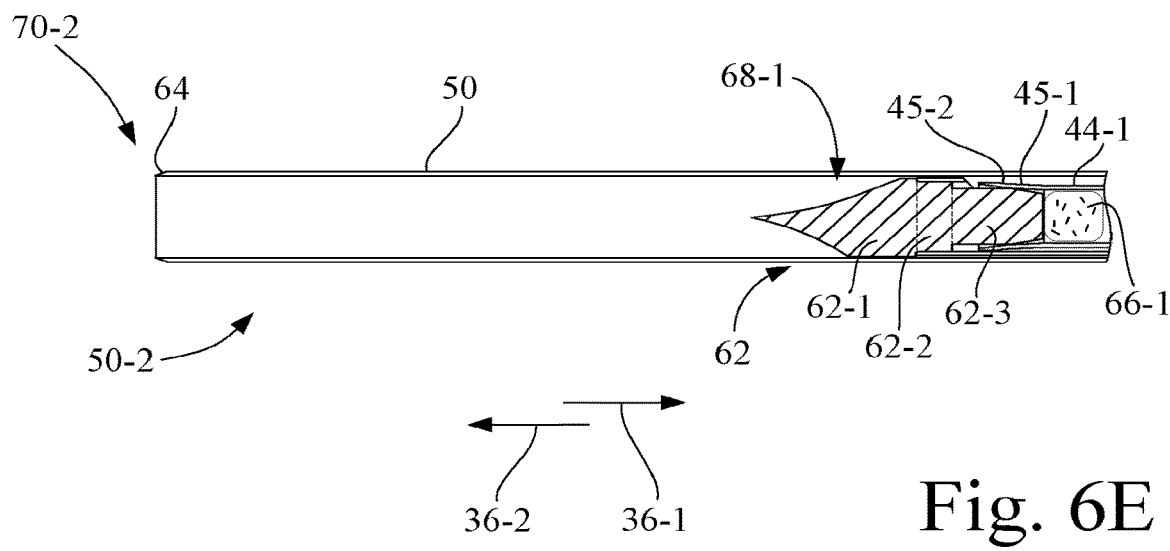
FIG. 6E shows the relative positions of the vacuum cannula, the stylet cannula, and the cutter cannula, wherein the stylet cannula is moved within the cutter cannula in the proximal direction to mechanically aid in moving the tissue sample into the flared portion of the vacuum cannula.
Figure 6F:
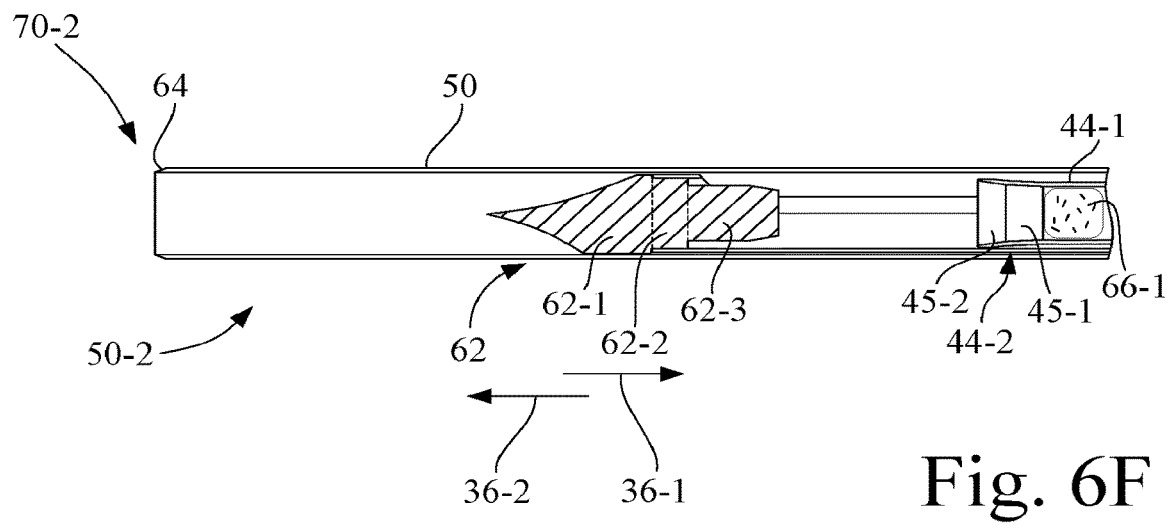
FIG. 6F shows the relative positions of the vacuum cannula, the stylet cannula, and the cutter cannula, wherein the stylet cannula is moved within the cutter cannula in the distal direction to disengage the protrusion member from the flared portion of the vacuum cannula.
Figure 6G:
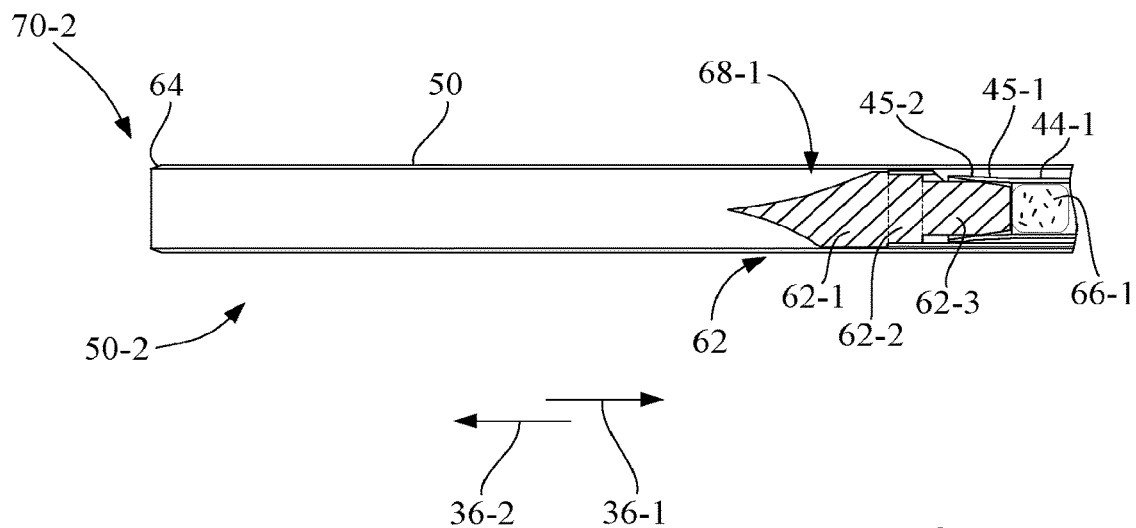
FIG. 6G shows the relative positions of the vacuum cannula, the stylet cannula, and the cutter cannula, wherein the stylet cannula is again moved within the cutter cannula in the proximal direction, such that the protrusion member re-engages the flared portion of the vacuum cannula.
Figure 6H:
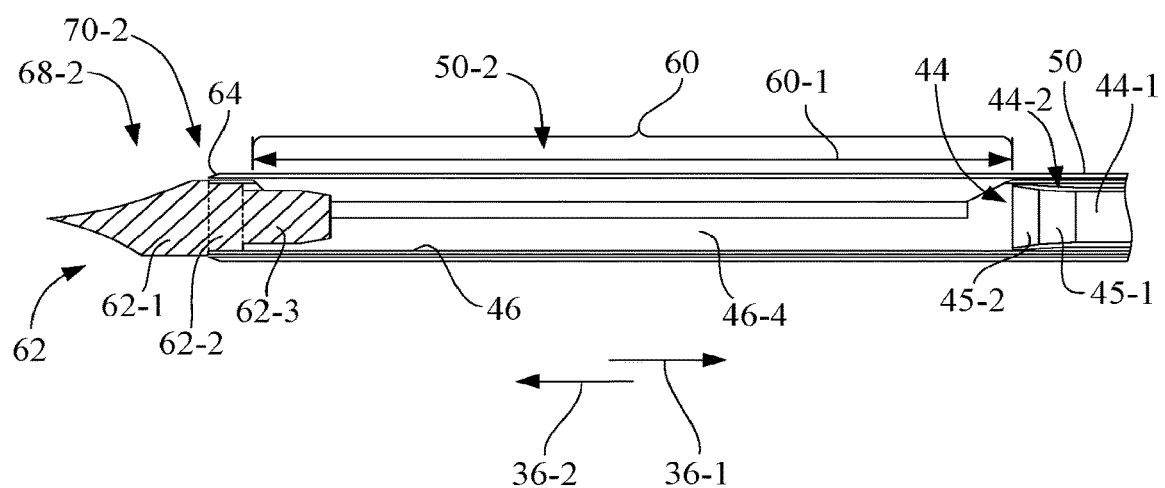
FIG. 6H shows the relative positions of the vacuum cannula, the stylet cannula, and the cutter cannula, wherein the stylet cannula is again moved within the cutter cannula in the distal direction to disengage the protrusion member from the flared portion of vacuum cannula and return to the extended position.

FIGS. 6A-6H collectively represent a tissue sample severing and transport sequence. FIGS. 6E and 6G show stylet cannula 46 in its retracted position 68-1. FIGS. 6A, 6B, and 6H show stylet cannula 46 in its extended position 68-2, sometimes also referred to as a zero position. FIGS. 6C, 6D, and 6F show stylet cannula 46 in various positions intermediate to retracted position 68-1 and extended position 68-2. FIGS. 6B and 6C show cutter cannula 50 in its retracted position 70-1, which exposes sample notch 60 of stylet cannula 46 when stylet cannula 46 is in or near its extended position 68-2. FIGS. 6A and 6D-6H show cutter cannula 50 in its extended position 70-2, sometimes also referred to as a zero position, wherein cutter cannula 50 covers the sample notch 60 of stylet cannula 46.

To effect the described movements of stylet cannula 46, controller circuit 18 executes program instructions and sends respective control signals to transport module 32 of driver assembly 12, which in turn transfers the motion to stylet gear-spindle set 48 of biopsy probe assembly 14. Likewise, to effect the described movements of cutter cannula 50, controller circuit 18 executes program instructions and sends respective control signals to cutter module 30 of driver assembly 12, which in turn transfers the motion to cutter gear-spindle set 52 of biopsy probe assembly 14. Controller circuit 18 may determine an axial position of each of stylet cannula 46 and cutter cannula 50, relative to the respective zero position, by counting the respective number of motor drive pulses, or alternatively, the respective number of motor shaft revolutions.

FIG. 6A shows the relative positions of vacuum cannula 44, stylet cannula 46, and cutter cannula 50 before, during, and immediately after the piercing shot effected by piercing module 34. As shown, distal portion 50-2 of cutter cannula 50 is extended over sample notch 60.

In the sequence step illustrated in FIG. 6B, vacuum source 22 is actuated to deliver a vacuum via vacuum cannula 44 to lumen 46-4 of stylet cannula 46 at sample notch 60, and cutter cannula 50 is retracted by actuation of cutter module 30 to expose sample notch 60, thereby permitting tissue 66 to be drawn into lumen 46-4 of stylet cannula 46 through sample notch 60. In the present embodiment, in order to expose sample notch 60, cutter cannula 50 rotates counter-clockwise to effect a linear translation of cutter cannula 50 in proximal direction 36-1 for a distance of approximately 23 millimeters (mm) to define the open length of sample notch 60. As used herein, the relative term "approximately" means the base value in the indicated units (if any) plus or minus five percent, unless stated otherwise. The actual aperture size at sample notch 60, corresponding to a desired sample size, may be user-selected at user interface 28, wherein a distance that cutter cannula 50 is retracted toward retracted position 70-1 from extended position 70-2 is controlled by controller circuit 18 to correspond to the sample size selected by the user.

FIGS. 6C and 6D illustrate a cutting sequence.

In the sequence step illustrated in FIG. 6C, in order to increase the size of tissue sample to be collected, stylet cannula 46 may be moved alternatingly in proximal direction 36-1 and distal direction 36-2 a short distance e.g., 2 to 5 mm, so as to shake sample notch 60, thereby increasing the amount of tissue 66 that passes through sample notch 60 and into lumen 46-4 of stylet cannula 46. The last move of the shake is defined to keep sample notch 60 in a 1 mm retracted position (see FIG. 6C) compared to the zero position of stylet cannula 46 as depicted in FIG. 6A. This is to ensure that cutter cannula 50 closes sample notch 60 during the cutting sequence (see FIG. 6D) and will cut 1 mm further, to thus ensure that connective tissue or strings are completely cut during the cutting sequence step illustrated in FIG. 6D.

In the cutting sequence step illustrated in FIG. 6D, cutter cannula 50 is rotated and translated in distal direction 36-2 to sever a tissue sample 66-1 from tissue 66. In the present embodiment, cutter cannula 50 rotates clockwise to effect a linear translation of cutter cannula in distal direction 36-2 for a distance of approximately 23 mm in order to cut the tissue and return to the zero position.

FIGS. 6E-6H illustrate a tissue sample transport sequence.

In the sequence step illustrated in FIG. 6E, vacuum is applied by vacuum cannula 44, and stylet cannula 46 is moved within cutter cannula 50 in proximal direction 36-1 to mechanically aid in moving tissue sample 66-1 into flared portion 44-2 of vacuum cannula 44. More particularly, as stylet cannula 46 is moved within cutter cannula 50 in proximal direction 36-1, protrusion member 62-3 of piercing tip 62 engages tissue sample 66-1 to assist tissue sample 66-1 into vacuum cannula 44. Protrusion member 62-3 then engages flared portion 44-2 of vacuum cannula 44 to close off an air inflow into flared portion 44-2 of vacuum cannula 44.

In the sequence step illustrated in FIG. 6F, with vacuum being applied by vacuum cannula 44, stylet cannula 46 is moved within cutter cannula 50 in distal direction 36-2 to disengage protrusion member 62-3 from the flared portion 44-2 of vacuum cannula 44 to cause an abrupt change in air flow into vacuum cannula 44, thereby helping the vacuum transport of tissue sample 66-1 through vacuum cannula 44.

The sequence steps illustrated in FIGS. 6G and 6H are essentially a repeat of sequence steps 6E and 6F.

In the sequence step illustrated in FIG. 6G, with vacuum applied to vacuum cannula 44 by vacuum source 22, stylet cannula 46 is again moved within cutter cannula 50 in proximal direction 36-1, such that protrusion member 62-3 of piercing tip 62 re-engages flared portion 44-2 of vacuum cannula 44 to again close off an air inflow into flared portion 44-2 of vacuum cannula 44.

In the sequence step illustrated in FIG. 6H, with vacuum being applied to vacuum cannula 44 by vacuum source 22, stylet cannula 46 is moved within cutter cannula 50 in distal direction 36-2 to again disengage protrusion member 62-3 from flared portion 44-2 of vacuum cannula 44 to cause an abrupt change in air flow into vacuum cannula 44, thereby helping the vacuum transport of tissue sample 66-1 (if not already delivered by sequence steps of FIGS. 6E and 6F) through vacuum cannula 44. At the end of the sequence of FIG. 6H, stylet cannula 46 is re-positioned at the tissue receiving position i.e., extended position 68-2, also referred to as the zero position, and is ready to receive tissue for a next tissue sample, in which the sequence steps of FIGS. 6A-6H would be repeated.

It is noted that the sample transport sequence illustrated in FIGS. 6E and 6F may be repeated as many times as necessary to complete the vacuum transport of tissue sample 66-1 through vacuum cannula 44. Also, the backward motion of protrusion member 62-3 of piercing tip 62 of stylet cannula 46 in proximal direction 36-1 may be implemented as incremental steps, alternating between a backward motion and then a forward motion (the forward distance being less than the backward distance) until the final position (retracted position 68-1) is reached, as depicted in FIGS. 6E and 6G.

Figure 7:
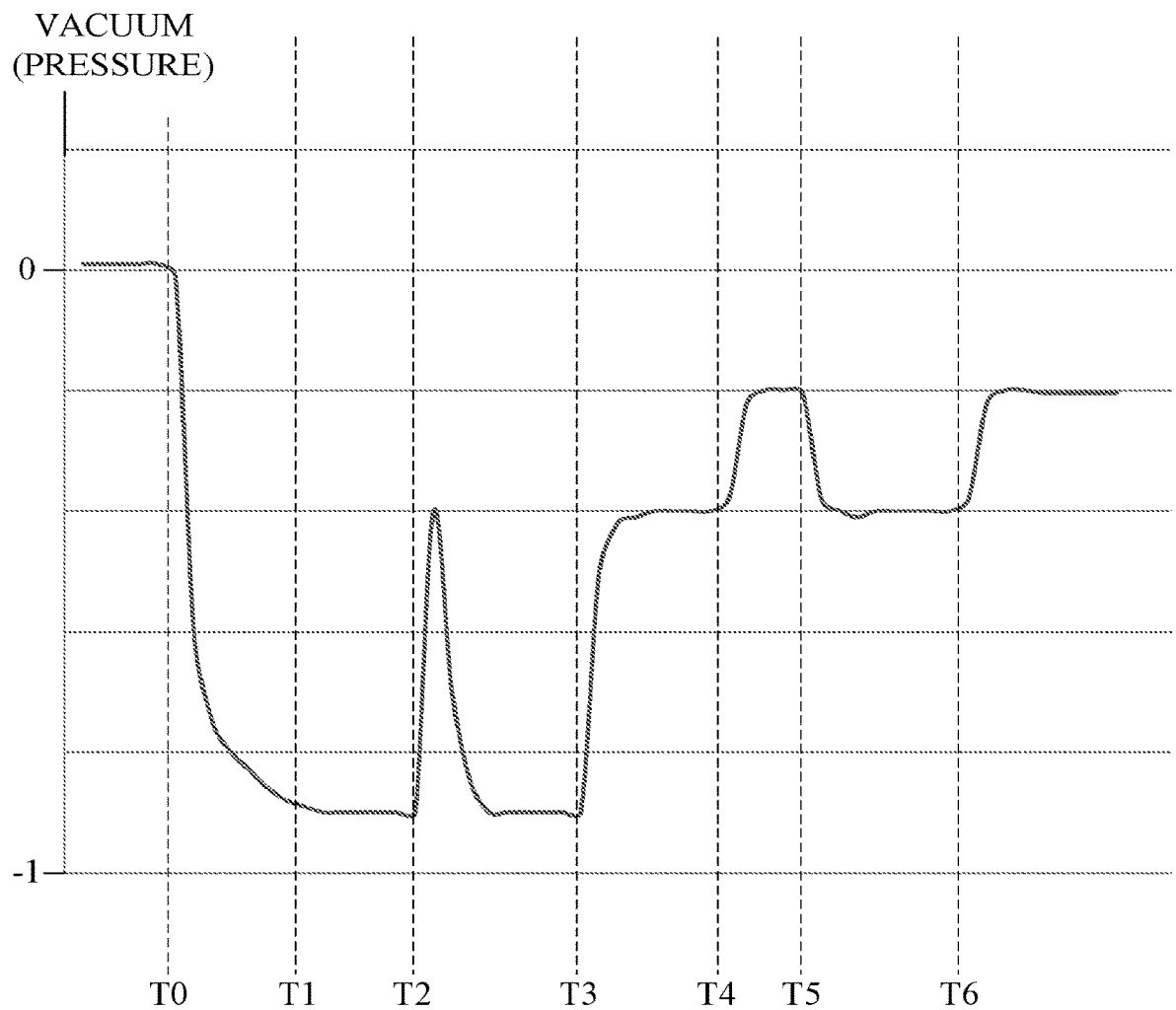
FIG. 7 is a vacuum/time graph depicting a baseline vacuum pressure at several different positions during a tissue sample cutting and transport sequence as depicted in FIGS. 6A-6H.

FIG. 7 is a vacuum graph depicting a baseline vacuum pressure at different positions during the tissue sample cutting and transport sequence depicted in FIGS. 6A-6H.

Referring to the vacuum graph of FIG. 7, it is noted that vacuum is applied throughout the entire sequence depicted in FIGS. 6A-6H. At time T0, vacuum source 22 is activated, and vacuum (negative pressure) builds in vacuum cannula 44. At time T1, maximum vacuum is achieved, which corresponds to the end of the cutting sequence step depicted in FIG. 6D. At time T2, the tissue stuffing sequence of FIGS. 6E-6F begins, and vacuum pressure abruptly drops due to a moment in which vent holes 80 in stylet cannula 46 are not restricted. Vacuum begins to build prior to time T3 as protrusion member 62-3 of piercing tip 62 approaches flared portion 44-2 of vacuum cannula 44, and maximizes, representing the end of the first stuffing sequence depicted in FIG. 6E. At time T3, vacuum pressure abruptly drops due to protrusion member 62-3 of piercing tip 62 being moved away from flared portion 44-2 as depicted in FIG. 6F. In some instances, tissue sample 66-1 may have been delivered to sample cup 56. At time T4, the second stuffing sequence depicted in FIGS. 6G and 6H begins. Time T5 corresponds to the end of the second stuffing sequence depicted in FIG. 6G. At time T6, vacuum pressure drops due to protrusion member 62-3 of piercing tip 62 again being moved away from flared portion 44-2 as depicted in FIG. 6H, and back to the tissue receiving (zero) position.

By comparing an actual vacuum pressure to the baseline vacuum graph depicted in FIG. 7 at different stages of the tissue cutting and transport sequence depicted in FIGS. 6A-6H, cutting or tissue transport anomalies can be identified and corrective action can be attempted.

In accordance with an aspect of the invention, vacuum sensor 24 provides vacuum pressure feedback signals to controller circuit 18, and controller circuit 18 executes program instructions to determine whether the actual vacuum pressure provided by vacuum sensor 24 deviates by more than a predetermined amount from the baseline pressure of the vacuum graph of FIG. 7 at a corresponding point in the tissue cutting and transport sequence. The predetermined amount may be, for example, the baseline vacuum pressure plus or minus 10 percent. If the deviation is outside the acceptable range of deviation, then corrective action may be taken depending upon when in the tissue cutting and transport sequence the anomaly occurred.

For example, if the vacuum pressure falls below the baseline by more than the allowable deviation during the time period between times T1 and T2, this may be an indication of an incomplete cut, and thus controller circuit 18 may repeat the cutting sequence depicted in FIGS. 6C and 6D without user intervention, rather than immediately going into an error state. Similarly, if the vacuum pressure rises above the baseline by more than the allowable deviation between the times T3 to T5, this may be an indication of an incomplete tissue transport through vacuum cannula 44, and thus controller circuit 18 may increase the number of iterations of sequence steps 6E and 6F without user intervention.

Referring again to FIG. 5A, vacuum is maintained in biopsy probe assembly 14 by a series of seals. A seal 72, e.g., a sleeve-type seal or O-ring arrangement, is located to provide a seal between cutter cannula 50 and stylet cannula 46. A seal 74, e.g., an O-ring, is located to provide a seal between stylet cannula 46 and vacuum cannula 44. A seal 76, e.g., a sleeve-type seal or O-ring arrangement, is located to provide a seal between vacuum cannula 44 and vacuum chamber portion 54-1 of sample manifold 54. Also, a seal 78 may be located in collection chamber portion 54-2 of sample manifold 54 and sample cup 56. Finally, a seal is placed at vacuum input port 54-3 at the vacuum interface between biopsy probe assembly 14 and driver assembly 12.

During operation, vacuum pump 22-2 of vacuum source 22 will build up vacuum (negative pressure) in the vacuum reservoir formed by sample manifold 54 and sample cup 56. More particularly, the volume of sample cup 56 and sample manifold 54 will define the strength of a "vacuum boost", and also defines the cycle time for vacuum pump 22-2 of vacuum source 22. In the present embodiment, for example, the volume is approximately 10 milliliters.

Regarding the "vacuum boost", stylet cannula 46 has one or more vent openings 80, e.g., annularly arranged, at a predetermined distance proximal from tip portion 62-1, and these vent openings 80 (see FIG. 4) will be exposed to the atmosphere when the stylet cannula 46 is retracted to retracted position 68-1 (see FIGS. 6E and 6G), wherein vent openings 80 slide under seal 72 between cutter cannula 50 and stylet cannula 46. Once these vent openings 80 are exposed to the atmosphere, the system is 'open' and the build-up vacuum pressure will be equalized with the surrounding pressure so as to create the vacuum boost effect, in addition to the continuous flow delivered by vacuum pump 22-2 of vacuum source 22.

Referring again to FIG. 3, when activating the cutter motor 30-1 for cutting tissue by moving cutter cannula 50 or activating transport motor 32-1 for transporting tissue by moving stylet cannula 46, each motor pulls current from battery 26. This current will linearly increase with load on the respective motor. Thus, the amount of current consumed can be translated into load. When working with dense tissue, the load may increase, and this is detected by monitoring the current using a current monitoring program executed by controller circuit 18.

Each of cutter motor 30-1 and transport motor 32-1 has a maximum continuous current rating (load) at which the motor can run indefinitely, and when the respective motor exceeds this continuous current (load), the motor can only run for a limited time before the motor is damaged (e.g., the windings burn in the motor), wherein the higher the load the shorter the time. The current monitoring program executed by controller circuit 18 monitors the current for each motor, and when the current exceeds the maximum continuous level for a respective motor, then it is determined that the motor has entered dense tissue, and driver assembly will go into a dense tissue mode.

When dense tissue is encountered, controller circuit 18 controls the current supplied to the respective motor to provide motor protection and to permit the motor current to exceed the maximum continuous current rating for short periods of time, based on the status (virtual energy level) of a virtual energy reservoir that is established in memory circuit 18-2 of controller circuit 18.

The idea is to exert as much strength of the motor as possible without damaging the motor windings, when such challenging dense tissue is encountered. Once the motor, e.g., cutter motor 30-1 and/or transport motor 32-1, starts running in any of the phases, the motor speed (revolutions per minute (rpm)) is set as 100% based on the voltage being set in controller circuit 18, e.g., to e.g. 6 volts, and then an increase in load (torque) will increase the current consumption and potentially slow down the motor until it stalls. Controller circuit 18 has the option of increasing the voltage from 6 volts to, e.g., 9 volts and by that increase the speed (rpm) and stall torque, and thus overcome more dense tissue. In the present example, it is assumed that each motor has three separate windings, or phases. It was recognized, however, that some very dense tissue could potentially stall the motor from rotating, and meanwhile only one of the motor phases or windings is in conduction, which will lead a dramatic temperature increase in this single phase and lead to burn-out of the motor. The virtual energy reservoir is used for monitoring the heat when running between continues torque level and stall torque level, where there is a risk to burn the motor windings.

In accordance with an aspect of the invention, it is possible to exceed the continuous current level, e.g., when encountering dense tissue, and still protect the motor without sacrificing motor performance.

It is assumed that each of the motor is initialized at rest, and the ambient temperature is the normal room temperature. By keep tracking of the instant current consumption over the operation time, a corresponding increment of motor winding temperature can be predicted. Thus, for dense tissue detection/motor protection, a virtual energy reservoir is established in memory circuit 18-2 for each motor cutter motor 30-1 and transport motor 32-1. The virtual energy reservoir can be filled up or drained at runtime based on integrating the difference of the actual motor winding current and the nominal motor winding current (maximum continuous current) over time. The motor winding temperature starts to increase when the actual motor winding current is higher than the nominal motor winding current (maximum continuous current), and vice versa.

Controller circuit 18 thus executes program instructions to predict when the winding temperature is above its thermal limit, and if so determined, controller circuit 18 will send control signals to the respective cutter module 30 or transport module 32 to lower the motor torque before the respective motor gets too hot. The algorithm executed as program instructions by controller circuit 18 is as follows:

$$\int (I^2 - I_n^2) t \text{ wherein: "I" represents the actual motor winding current;}$$

"In" represents the nominal current of the motor windings; and

"t" represent time.

Figure 8A:
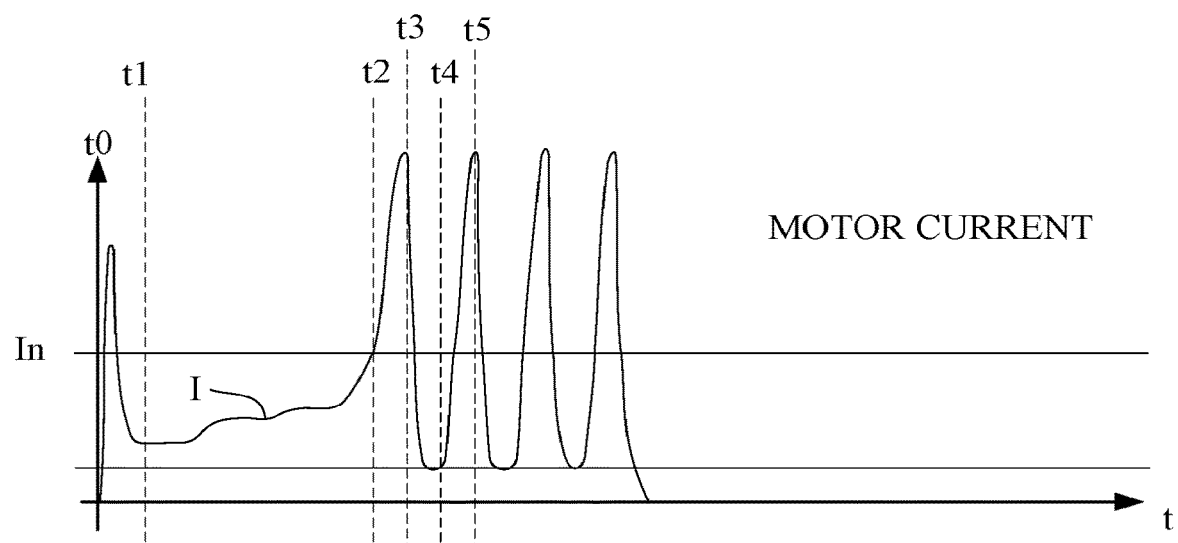
FIG. 8A is a graph of actual motor winding current (I) of a motor of the driver assembly of FIG. 1, to be viewed in conjunction with the graph of FIG. 8B.
Figure 8B:
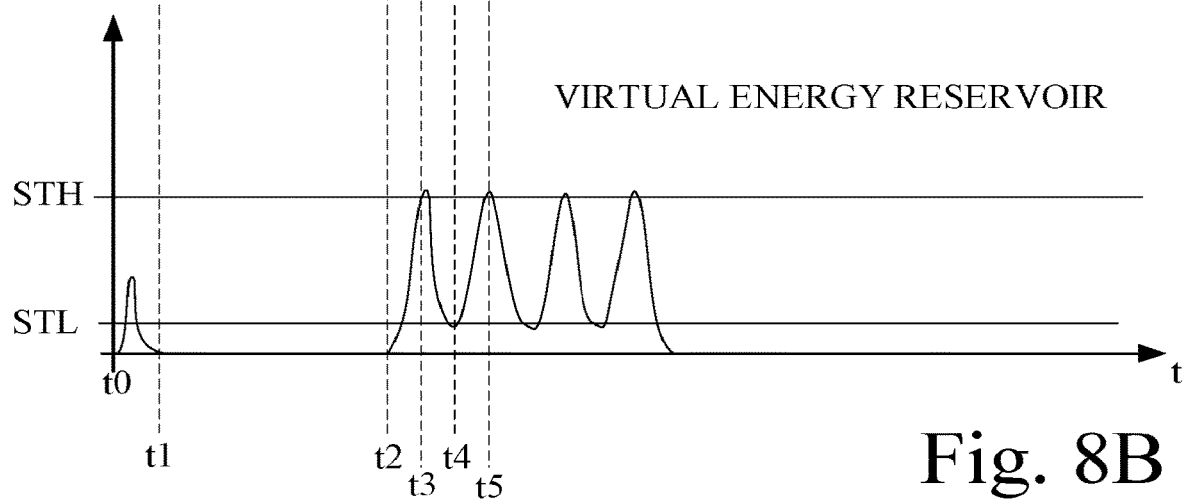
FIG. 8B is a graph of the energy status of a virtual energy reservoir established in a memory circuit of the driver assembly of FIG. 1, to be viewed in conjunction with the graph of FIG. 8A.

FIG. 8A is a graph of actual motor winding current (I), and FIG. 8B is a graph of the energy status of the virtual energy reservoir established in memory circuit 18-2. In the graph of FIG. 8B, STH represents the upper threshold and STL represents the lower threshold of the virtual energy reservoir.

Referring to FIGS. 8A and 8B in combination, when the motor starts running from t0, there is a huge current spike for the motor to accelerate, at the same time, the virtual energy reservoir starts to be filled though it has not exceeded the upper threshold. The virtual energy reservoir is empty at t1, and the virtual energy reservoir continues being zero until the current abruptly increases again at t2. When the energy accumulation in the virtual energy reservoir is over the upper threshold STH for the first time at t3, then controller circuit 18 takes immediate action to reduce the current supplied to the respective motor to a safe level (predefined). The virtual energy reservoir level begins to drop from then on, even though the virtual energy reservoir level has been experienced with a very short overshooting. When the energy accumulation of the virtual energy reservoir level drops below the lower threshold STL at t4, then controller circuit 18 takes immediate action to increase, i.e., boost, the current again. The same process may be repeated three times before controller circuit 18 designates the condition as an error condition, meaning that the tissue is significantly dense, i.e., too dense to be cut. The three repeated times before error is predefined in the software executed by controller circuit 18. The number of repetitions may be varied, if desired, based at least in part on the length of the cycle time (e.g., the time of t5-t3).

In the present embodiment, the dense tissue mode is entered automatically when driver assembly 12 is powered on, and runs all the time after driver assembly 12 has been powered.

The following items also relate to the invention:

In one form, the invention relates to a biopsy apparatus that includes a driver assembly and a biopsy probe. The driver assembly has an electromechanical power source and a vacuum source. The biopsy probe assembly is releasably attached to the driver assembly. The biopsy probe assembly has a vacuum cannula and a stylet cannula coaxially arranged along a longitudinal axis. The vacuum cannula is positioned inside the stylet cannula. The vacuum cannula is coupled in fluid communication with the vacuum source. The vacuum cannula has an elongate portion and a flared portion that extends distally from the elongate portion. The stylet cannula is coupled in driving communication with the electromechanical power source. The stylet cannula is movable relative to the vacuum cannula between a first extended position and a first retracted position. The stylet cannula has a proximal portion and a distal portion. The distal portion has a sample notch and a protrusion member that extends proximally in a lumen of the stylet cannula along a portion of a longitudinal extent of the sample notch. When the stylet cannula is in the first retracted position, the protrusion member is received within the flared portion of the vacuum cannula.

The flared portion of the vacuum cannula may have a first flared stage that diverges from the elongate portion at a first acute angle relative to the elongate portion, and a second flared stage that diverges from the first flared stage at a second acute angle relative to the elongate portion. Optionally, the second acute angle is larger than the first acute angle.

The biopsy probe assembly may further include a cutter cannula coaxial with the stylet cannula and the vacuum cannula, wherein the stylet cannula is positioned within the cutter cannula. The cutter cannula is movable relative to the stylet cannula between a second extended position to cover the sample notch and a second retracted position to expose the sample notch when the stylet cannula is in the first extended position.

In any of the embodiments, the driver assembly optionally includes a driver housing that has a front surface. The biopsy probe assembly has a probe housing with an elongate portion, and in any of the embodiments, may include a front plate. When the biopsy probe assembly is attached to the driver assembly, the front plate is positioned distally adjacent to an entirety of the front surface of the driver housing so as to shield the entirety of the front surface of the driver assembly from contact with a patient.

In any of the embodiments, the driver assembly may include a controller circuit and an electromechanical power source. The controller circuit is electrically and communicatively coupled to the electromechanical power source. The electromechanical power source has a cutter module and a transport module. The cutter module has a first motor and the transport module has a second motor. When the biopsy probe assembly is attached to the driver assembly, the cutter module is drivably coupled to the cutter cannula and the transport module is drivably coupled to the stylet cannula. Each of the first motor and the second motor has a maximum continuous current rating at which the respective motor can run indefinitely. The controller circuit is configured to execute program instructions to control the current for each of the first motor and the second motor. The controller circuit is configured to determine that the motor has entered dense tissue, when the current exceeds the maximum continuous level for a respective motor.

In any of the embodiments having a controller circuit, the controller circuit may include a processor circuit and memory circuit, and may have a virtual energy reservoir established in the memory circuit for each of the first motor and the second motor. The processor is configured to execute program instructions to control the current supplied to a respective motor to provide motor protection and to permit the respective motor current to exceed the maximum continuous current rating for short periods of time, based on the status of the virtual energy reservoir.

In any of the embodiments having at least one virtual energy reservoir, each virtual energy reservoir can be filled up or drained. The controller circuit may be configured to integrate a difference between an actual motor winding current for a respective motor and the maximum continuous current rating over time. The controller circuit may be configured to take action to reduce the current supplied to the respective motor, when an energy accumulation level in the virtual energy reservoir is over an upper threshold. The controller circuit may be configured to take action to increase the current supplied to the respective motor, when the energy accumulation level of the virtual energy reservoir level drops below a lower threshold. The apparatus may be controlled such that when an energy accumulation level in the virtual energy reservoir is over an upper threshold, the controller circuit then takes action to reduce the current supplied to the respective motor. The apparatus may be controlled such that when the energy accumulation level of the virtual energy reservoir level drops below a lower threshold, the controller circuit then takes action to increase the current supplied to the respective motor.

In any of the embodiments having a controller circuit, the controller circuit may be configured to execute program instructions to repeatedly move the protrusion member of the stylet cannula into and away from the flared portion of the vacuum cannula to aid in delivering a tissue sample into the flared portion of the vacuum cannula. The apparatus may be controlled such that vacuum may be continuously applied to the vacuum cannula during the time that the protrusion member of the stylet cannula is repeatedly moved into and away from the flared portion of the vacuum cannula.

In another form, the invention relates to a biopsy apparatus having a driver assembly that has an electromechanical power source, a vacuum source, and a controller circuit electrically and communicatively coupled to the electromechanical power source and to the vacuum source. A biopsy probe assembly is releasably attached to the driver assembly. The biopsy probe assembly has a vacuum cannula, a stylet cannula, and a cutter cannula coaxially arranged along a longitudinal axis. The vacuum cannula is positioned inside the stylet cannula. The stylet cannula is positioned inside the cutter cannula. The vacuum cannula is coupled in fluid communication with the vacuum source. The vacuum cannula has an elongate portion and a flared portion that extends distally from the elongate portion. The stylet cannula is coupled in driving communication with the electromechanical power source. The stylet cannula is movable relative to the vacuum cannula between a first extended position and a first retracted position. The stylet cannula has a proximal portion and a distal portion. The distal portion has a sample notch and a protrusion member that extends proximally in a lumen of the stylet cannula along a portion of a longitudinal extent of the sample notch. When the stylet cannula is in the retracted position, the protrusion member is received within the flared portion of the vacuum cannula. The cutter cannula is coupled in driving communication with the electromechanical power source. The cutter cannula is movable relative to the stylet cannula between a second extended position to cover the sample notch and a second retracted position to expose the sample notch when the stylet cannula is in the first extended position.

The controller circuit may be configured to execute program instructions to control the apparatus such that the protrusion member of the stylet cannula is repeatedly moved into and away from the flared portion of the vacuum cannula to aid in delivering a tissue sample into the flared portion of the vacuum cannula. The apparatus may be controlled such that vacuum is continuously applied to the vacuum cannula during the time that the protrusion member of the stylet cannula is repeatedly moved into and away from the flared portion of the vacuum cannula.

The electromechanical power source may include a cutter module and a transport module. The cutter module has a first motor and the transport module has a second motor. When the biopsy probe assembly is attached to the driver assembly, the cutter module is drivably coupled to the cutter cannula and the transport module is drivably coupled to the stylet cannula.

Each of the first motor and the second motor has a maximum continuous current rating at which the respective motor can run indefinitely. The controller circuit is configured to execute program instructions to control the current for each of the first motor and the second motor. The controller circuit may be configured to determine that the motor has entered dense tissue, when the current exceeds the maximum continuous level for a respective motor.

The controller circuit may include a processor circuit and memory circuit. The controller circuit may have a virtual energy reservoir established in the memory circuit for each of the first motor and the second motor. The processor may be configured to execute program instructions to control the current supplied to a respective motor to provide motor protection and to permit the respective motor current to exceed the maximum continuous current rating for short periods of time, based on the status of the virtual energy reservoir.

In any of the embodiments having at least one virtual energy reservoir, each virtual energy reservoir can be filled up or drained. The controller circuit is configured to integrate a difference between an actual motor winding current for a respective motor and the maximum continuous current rating over time. The controller circuit may be configured to reduce the current supplied to the respective motor, when an energy accumulation level in the virtual energy reservoir is over an upper threshold. The controller circuit may be configured to increase the current supplied to the respective motor, when the energy accumulation level of the virtual energy reservoir level drops below a lower threshold. The apparatus may be controlled such that when an energy accumulation level in the virtual energy reservoir is over an upper threshold, the controller circuit then takes action to reduce the current supplied to the respective motor. The apparatus may be controlled such that when the energy accumulation level of the virtual energy reservoir level drops below a lower threshold, the controller circuit then takes action to increase the current supplied to the respective motor.

The flared portion of the vacuum cannula may have a first flared stage that diverges from the elongate portion at a first acute angle relative to the elongate portion, and a second flared stage that diverges from the first flared stage at a second acute angle relative to the elongate portion. Optionally, the second acute angle is larger than the first acute angle.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A method of using a biopsy apparatus, comprising:
   moving a stylet cannula relative to a vacuum cannula between a first extended position and a first retracted position; and
   receiving a protrusion member of the stylet cannula within a flared portion of the vacuum cannula when the stylet cannula is in the first retracted position.

2. The method of claim 1, comprising moving a cutter cannula relative to the stylet cannula between a second extended position to cover the sample notch and a second retracted position to expose a sample notch of the stylet cannula when the stylet cannula is in the first extended position.

3. The method of claim 1, comprising repeatedly moving the protrusion member of the stylet cannula into and away from the flared portion of the vacuum cannula.

4. A method of using a biopsy apparatus, comprising:
   providing a driver assembly having an electromechanical power source and a vacuum source;
   providing a biopsy probe assembly releasably attached to the driver assembly, the biopsy probe assembly having a vacuum cannula and a stylet cannula coaxially arranged along a longitudinal axis, with the vacuum cannula being positioned inside the stylet cannula, the vacuum cannula being coupled in fluid communication with the vacuum source, the vacuum cannula having an elongate portion and a flared portion that extends distally from the elongate portion, the stylet cannula being coupled in driving communication with the electromechanical power source, the stylet cannula having a proximal portion and a distal portion, the distal portion having a sample notch and a protrusion member that extends proximally in a lumen of the stylet cannula along a portion of a longitudinal extent of the sample notch;
   moving the stylet cannula relative to the vacuum cannula between a first extended position and a first retracted position; and
   receiving the protrusion member within the flared portion of the vacuum cannula when the stylet cannula is in the first retracted position.

5. The method of claim 4, wherein the flared portion of the vacuum cannula has a first flared stage that diverges from the elongate portion at a first acute angle relative to the elongate portion, and a second flared stage that diverges from the first flared stage at a second acute angle relative to the elongate portion, wherein the second acute angle is larger than the first acute angle.

6. The method of claim 4, wherein the biopsy probe assembly includes a cutter cannula coaxial with the stylet cannula and the vacuum cannula, the stylet cannula being positioned within the cutter cannula, the method further comprising:
moving the cutter cannula relative to the stylet cannula between a second extended position to cover the sample notch and a second retracted position to expose the sample notch when the stylet cannula is in the first extended position.

7. The method of claim 4, the driver assembly including a driver housing having a front surface, and the biopsy probe assembly having a probe housing having an elongate portion and a front plate, the method further comprising:
attaching the biopsy probe assembly to the driver assembly; and
shielding the entirety of the front surface of the driver assembly with the front plate.

8. The method of claim 4, wherein the driver assembly comprises a controller circuit electrically and communicatively coupled to the electromechanical power source, and the electromechanical power source has a cutter module and a transport module, the cutter module having a first motor and the transport module having a second motor, the method further comprising drivably coupling the cutter module to the cutter cannula and drivably coupling the transport module to the stylet cannula.

9. The method of claim 8, wherein each of the first motor and the second motor has a maximum continuous current rating, the method comprising:
controlling the current for each of the first motor and the second motor; and
determining that the motor has entered dense tissue when the current exceeds the maximum continuous current rating for a respective motor.

10. The method of claim 8, comprising:
establishing a virtual energy reservoir in a memory circuit for each of the first motor and the second motor;
controlling the current supplied to a respective motor to provide motor protection; and
permitting the respective motor current to exceed the maximum continuous current rating for short periods of time, based on a status of the virtual energy reservoir.

11. The method of claim 10, wherein each virtual energy reservoir is configured to be filled up or drained, the method comprising integrating a difference between an actual motor winding current for a respective motor and the maximum continuous current rating, over time, wherein when an energy accumulation level in the virtual energy reservoir is over an upper threshold, then reducing the current supplied to the respective motor, and when the energy accumulation level of the virtual energy reservoir level drops below a lower threshold, then increasing the current supplied to the respective motor.

12. The method of claim 4, comprising repeatedly moving the protrusion member of the stylet cannula into and away from the flared portion of the vacuum cannula to aid in delivering a tissue sample into the flared portion of the vacuum cannula.

13. The method of claim 12, comprising continuously applying vacuum to the vacuum cannula during the time that the protrusion member of the stylet cannula is repeatedly moved into and away from the flared portion of the vacuum cannula.

14. A method of using a biopsy apparatus, comprising:
providing a driver assembly having an electromechanical power source, a vacuum source, and a controller circuit electrically and communicatively coupled to the electromechanical power source and to the vacuum source;
providing a biopsy probe assembly releasably attached to the driver assembly, the biopsy probe assembly having a vacuum cannula, a stylet cannula, and a cutter cannula coaxially arranged along a longitudinal axis, with the vacuum cannula being positioned inside the stylet cannula, and the stylet cannula being positioned inside the cutter cannula;
coupling the vacuum cannula in fluid communication with the vacuum source, the vacuum cannula having an elongate portion and a flared portion that extends distally from the elongate portion;
coupling the stylet cannula in driving communication with the electromechanical power source, the stylet cannula being movable relative to the vacuum cannula between a first extended position and a first retracted position, the stylet cannula having a proximal portion and a distal portion, the distal portion having a sample notch and a protrusion member that extends proximally in a lumen of the stylet cannula along a portion of a longitudinal extent of the sample notch;
coupling the cutter cannula in driving communication with the electromechanical power source;
receiving the protrusion member within the flared portion of the vacuum cannula when the stylet cannula is in the retracted position; and
moving the cutter cannula relative to the stylet cannula between a second extended position to cover the sample notch and a second retracted position to expose the sample notch when the stylet cannula is in the first extended position.

15. The method of claim 14, the method comprising:
repeatedly moving the protrusion member of the stylet cannula into and away from the flared portion of the vacuum cannula to aid in delivering a tissue sample into the flared portion of the vacuum cannula; and
continuously applying vacuum to the vacuum cannula during the time that the protrusion member of the stylet cannula is repeatedly moved into and away from the flared portion of the vacuum cannula.

16. The method of claim 14, the electromechanical power source having a cutter module and a transport module, the cutter module having a first motor and the transport module having a second motor, the method comprising: drivably coupling the cutter module to the cutter cannula and drivably coupling the transport module to the stylet cannula.

17. The method of claim 16, wherein each of the first motor and the second motor has a maximum continuous current rating, the method comprising:
controlling the current for each of the first motor and the second motor; and
determining that the motor has entered dense tissue when the current exceeds the maximum continuous current rating for a respective motor.

18. The method of claim 16, comprising:
establishing a virtual energy reservoir established in a memory circuit for each of the first motor and the second motor;
controlling the current supplied to a respective motor to provide motor protection; and
permitting the respective motor current to exceed the maximum continuous current rating for short periods of time, based on the status of the virtual energy reservoir.

19. The method of claim 18, comprising integrating a difference between an actual motor winding current for a respective motor and a maximum continuous current rating, over time, wherein when an energy accumulation level in the virtual energy reservoir is over an upper threshold, then reducing the current supplied to the respective motor, and when the energy accumulation level of the virtual energy reservoir level drops below a lower threshold, then increasing the current supplied to the respective motor.

20. The method of claim 14, wherein the flared portion of the vacuum cannula has a first flared stage that diverges from the elongate portion at a first acute angle relative to the elongate portion, and a second flared stage that diverges from the first flared stage at a second acute angle relative to the elongate portion, wherein the second acute angle is larger than the first acute angle.

\* \* \* \* \*